United States Patent [19]

Van Houten

[11] Patent Number: 5,989,816
[45] Date of Patent: Nov. 23, 1999

[54] METHOD TO DETECT DNA DAMAGE AND MEASURE DNA REPAIR RATE

[75] Inventor: Bennett Van Houten, Galveston, Tex.

[73] Assignee: Research Development Foundation, Carson City, Nev.

[21] Appl. No.: 08/875,646

[22] PCT Filed: Jan. 29, 1996

[86] PCT No.: PCT/US96/01127

§ 371 Date: Jul. 31, 1997

§ 102(e) Date: Jul. 31, 1997

[87] PCT Pub. No.: WO96/23895

PCT Pub. Date: Aug. 8, 1996

Related U.S. Application Data

[63] Continuation-in-part of application No. 08/384,107, Feb. 1, 1995, abandoned.

[51] Int. Cl.⁶ .............................. C12Q 1/68; C12P 19/34; C07H 21/00
[52] U.S. Cl. .......................... 435/6; 435/91.2; 536/24.33
[58] Field of Search ...................... 435/91.2, 6; 536/22.1

[56] References Cited

U.S. PATENT DOCUMENTS 5,891,682   4/1999   Yoshida et al. .

OTHER PUBLICATIONS

Casou et al. Repair synthesis by human cell extracts in cisplatin–damaged DNA is preferentially determined by minor adducts Nucleic Acids Research vol. 20(23), pp. 6363–6368, 1992.

Piette, J. Biological consequences associated with DNA oxidation mediated by singlet oxygen J. Photochem, Photobiol. B: Biol., vol. 11, pp. 241–260, 1991.

Kalinowski et al. Analysis of DNA damage and repair in murine leukemina L1210 cells using a quantitative polymerase chain reaction assay, Nucleic Acid Research, vol. 20 (13), pp. 3485–3494, 1992.

*Primary Examiner*—Kenneth R. Horlick
*Assistant Examiner*—Jeffrey Siew
*Attorney, Agent, or Firm*—Benjamin Aaron Adler

[57] ABSTRACT

The present invention includes an improved method to detect and quantitatively assay the amount of DNA damage in large double-stranded templates starting with less than 50 ng of sample DNA. This invention has utility in vivo for quantitating gene-specific DNA damage, measuring DNA repair rates and monitoring efficacy of anti-neoplasia therapy in patients. Additionally, this invention is useful to detect and assess risk due to mutagenic environmental hazard sites, and monitor hazard site dynamics and includes a device for accomplishing these objects.

5 Claims, 24 Drawing Sheets

| Fragment size | Rel. Amp | Lesions/Fragment | Lesions/kb |
|---|---|---|---|
| 2.7 kb | 0.69±0.015 | 0.38±0.013 | 0.139±0.008 |
| 6.25 kb | 0.40 | 0.92 | 0.147 |
| 13.5 kb | 0.125 | 2.09 | 0.154 |
| 15.4 kb | 0.15±0.005 | 1.98±0.023 | 0.123±0.002 |
| 17.7 kb | 0.08±0.01 | 2.51±0.10 | 0.142±0.009 |
| 24 kb | 0.11 | 2.20 | 0.09 |

FIG. 4

| Fragment size | UV Dose (J/M²) | | | | | | | | | |
|---|---|---|---|---|---|---|---|---|---|---|
| | 0 | | 25 | | 5 | | 10 | | 20 | |
| | Rel. Amp | Lesion/kb | Rel.Amp | Lesions/kb | Rel.Amp | Lesions/kb | Rel.Amp | Lesions/kb | Rel.Amp | Lesions/kb |
| 6.25kb | 1.00 | 0 | 0.65±0.12 | 0.0072±0.0029 | 0.70±0.16 | 0.0058±0.0035 | 0.56±0.13 | 0.0095±0.0039 | 0.28±0.08 | 0.21±0.05 |
| 15.4kb | 1.00 | 0 | 0.61±0.24 | 0.0035±0.0023 | 0.40±0.02 | 0.0059±0.00004 | 0.27±0.02 | 0.0085±0.00004 | 0.08±0.002 | 0.16±0.0017 |
| 17.7kb | 1.00 | 0 | 0.692±0.027 | 0.0024±0.0021 | 0.47±0.06 | 0.0045±0.00066 | 0.26±0.005 | 0.0079±0.0010 | 0.073±0.005 | 0.16±0.004 |

FIG. 9

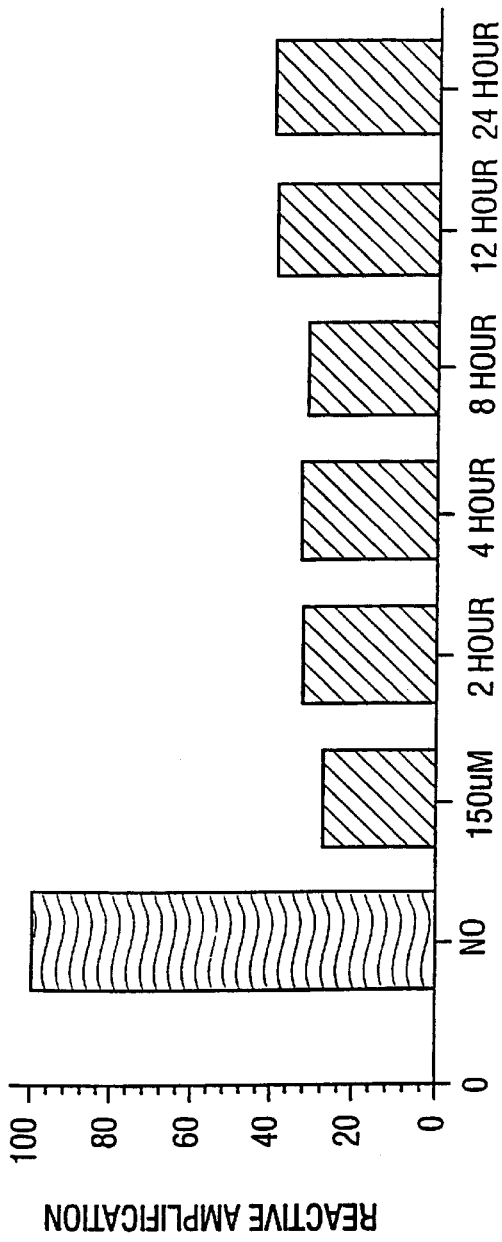
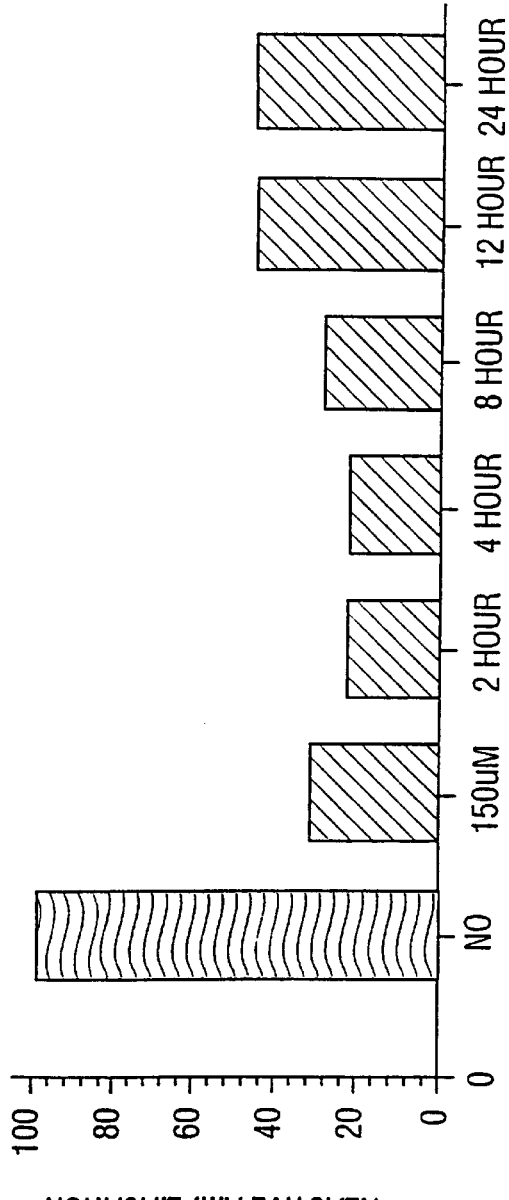

METHOD TO DETECT DNA DAMAGE AND MEASURE DNA REPAIR RATE

This application is a continuation-in-part of U.S. Ser. No. 08/384,107, Feb. 1, 1995 now abandoned.

FIELD OF THE INVENTION

This invention relates to the field of molecular biology and biochemistry. More specifically, it relates to detecting and quantitating DNA damage in animals and in cell culture, for monitoring the dynamics of DNA damage including rate of occurrence and remediation by DNA repair enzymes, and for detecting and assessing genotoxic risk in the environment.

BACKGROUND

Organisms are being constantly bombarded by endogenous and exogenous genotoxic agents which injure their DNA. This DNA damage, if left unrepaired, can lead to cell death, somatic mutations or cellular transformation, which at the organismal level can result in cancer, aging, and decreased immunocompetency. There is now a large amount of evidence which indicates that the repair of specific DNA lesions does not occur equally throughout the entire genome. For example, it has been shown that the DNA of actively transcribed regions is repaired more efficiently than DNA of inactive regions. This gene-specific DNA repair is due mainly to the rapid repair of the transcribed strand of actively expressed genes (Mellon et al., 1987; Mellon and Hanawalt, 1989; Smerdon and Thoma, 1990), and as a consequence can lead to the accumulation of mutations in the more slowly repaired non-transcribed strand (Chandrasekhar and Van Houten, 1994).

Preferential repair of DNA damage in actively transcribed genes was initially identified using a Southern hybridization-based assay employing T4 endonuclease V, which specifically cleaves DNA at pyrimidine dimer sites (Bohr and Okumoto, 1988). While this methodology has proven useful in the identification and study of gene-specific repair, it has the serious disadvantage of requiring a lesion-specific endonuclease to incise the DNA near the damaged nucleotide. Other disadvantages including:

- the requirements of relatively large amounts of starting sample DNA; and
- the need for specific restriction sites flanking the DNA region of interest.

Another approach to determining DNA damage and repair in specific genomic DNA regions is the Taq enzyme and polymerase chain reaction (PCR) method of Govan et al., (Govan et al., 1990). This method is based on the fact that many DNA lesions can block Taq DNA polymerase, which causes in a decrease in amplification product. The method of Govan et al., however, was not very powerful because of the small size limitation on the DNA segments being amplified—less than 450 bp. Subsequently, the sensitivity such assays was increased to DNA segments of about 2 to 3 kb (Jennerwein and Eastman, 1991; Kalinowski et al., 1992). Presently the detection of DNA damage in specific gene sequences of bacterial and mammalian cells is limited to the quantitation of amplification products ranging in size from 334 bp to 3.2 kb.

Limitation on the Sensitivity of Prior Art Amplification Assays

Current PCR assay methods are not sufficient to detect DNA damage after exposure to biologically and environmentally relevant doses of genotoxic agents, including ionizing radiation. While the current PCR-based assay for the detection of DNA damage appears to be useful at high doses of damaging agent, it suffers from lack of sensitivity at biologically relevant doses, and therefore can not be used reliably for accurate DNA damage detection and determining DNA repair rates in humans. This is a major problem as the art currently stands. To meet these needs, the sensitivity of a DNA damage detection assay must be increased from a current detection limit of about one lesion/$10^4$ nucleotides to one lesion/$10^5$ nucleotides.

DEFINITIONS

Amplification products—are the duplicates of the template's undamaged complementary DNA strands which are detected after the amplification process.

DNA damage—is modification of a bases or sugar moiety of DNA such that the replication of the DNA sequence is interrupted at the damage site.

Gene-specific—means that the DNA involved is associated with a known gene.

Genotoxin, genotoxic agent—is any agent that directly or indirectly damages DNA. These include compounds that arise in the cell naturally, or are directly derive from the environment, or indirectly from exposure to a agent in the environment (such as another compound or ionizing radiation). May also be called a mutagen.

Quantitative long-DNA amplification—refers to the amplification of long (>5,000 base pair) DNA templates to yield substantially only amplification products representing the intact (undamaged) complementary strands of the starting template sample.

Template—is a double-stranded DNA that contains at least one specific primer site on each of its complementary DNA strands separated by at least 5,000 base pairs on the intact template.

SUMMARY OF THE INVENTION

The present invention expands on the current art of this field in a number of important areas: 1) by establishing the conditions necessary for successfully accomplishing quantitative long-DNA amplification, i.e., greater than 5,000 base-pairs of DNA, 2) by improving sensitivity for the detection of DNA damage, 3) enabling the determination of the rate of DNA repair following a biologically relevant exposure to a genotoxic agent, including ionizing radiation, and 4) providing a means for detecting environmental hazards at the genetic level and for monitoring exposure to genotoxic agents. Additionally, the present invention does not require damage-specific endonucleases, and can yield information on the repair of several genes concurrently, and expands the ability of this art field to quantitate DNA amplification products and to detect one damaged lane in $10^5$ DNA nucleotides.

A further advantage of the present invention is that it requires significantly less starting sample to detect gene-specific DNA damage than current Southern-based methods, with about a 50 to 100 fold or greater improvement in sensitivity because the present method only requires as little as 5 ng to about 15 ng of starting double-stranded DNA template sample.

An additional advantage is that more than one template sample may be assayed in the same quantitative amplification reaction. This allows the use of an internal control in the reaction process as well as the simultaneous processing of multiple different template samples.

The present invention involves a method of detecting DNA damage in a double-stranded DNA template by having the complementary strands of the template each have a strand-specific primer site separated by at least about 5,000 base pairs in the double-stranded DNA template molecule; combining the complementary strands of the DNA template in a mixture with primers to the strand-specific primer-site on each of the complementary strands; performing quantitative long-DNA amplification on the mixture to produce amplification products; and detecting DNA damaged of the double-stranded DNA in the template sample in its amplification products. An aspect of this method is that where the double-stranded DNA template is a gene-specific sequence of genomic DNA, the method detects gene-specific DNA damage. A further aspect of this invention is the quantitation of DNA damage, wherein, the relative amount of damaged DNA in the original template sample is quantitatively related to the inverse of the amount of amplification product from the reaction.

The present invention also includes a method for determining the rate of DNA repair in a living organism or in tissue culture cells by taking double-stranded DNA template samples from the system at different times, processing each sample separately; quantitating the amount of DNA amplification from each sample; and using the change in the amount of DNA amplificaiton to determine the levels of DNA damate over time to assess the rate of DNA repair in the system.

The invention comprises a method for diagnosing efficacy of an anti-neoplasia therapy in a patient by determining the rate of DNA repair in a patient at at least two different times, and then diagnosing the efficacy of the therapy in the patient by comparing the individual rates of repair to assess the dynamics of the rates of repair over the course of time.

The present invention may be seen as including a device for detecting the presence of environmental genotoxic agents by detecting their effect at the genetic level. This may be accomplished by having at least two double-stranded DNA template samples with at least one of the template samples exposed to the environment (the test sample) and at least one of the template samples protected from the environment (the control sample). Another aspect of the instant device is a personal DNA mutagen exposure dosimeter with a means for attaching the dosimeter to a person, and additionally, a method of monitoring an individual's exposure to DNA mutagens over an interval of time by attaching the dosimeter to the individual for an interval of time, and then processing the device to detect DNA damage. The individual's exposure to genotoxins or DNA mutagens may then be monitored.

The invention further involves a method of detecting the presence of genotoxins (mutagens) in the environment by placing the device in an environment for a period of time effective to expose the environmental test sample to the mutagenic effects of any genotoxins present; processing the template DNA samples of the device to detect DNA damage; comparing the DNA damage in the control sample to the environmental sample to detect the presence of genotoxins in the environment. A further aspect of this object of the invention is a method of assessing the level of risk due to exposure to a mutagenic hazard in an environment by using the instant device and comparing the quantity of DNA damage in the control sample to the test sample.

An additional aspect of the invention is a method for mapping an environmental mutagen hazard site by placing the instant device at various map locations at the site for an effective period of time; processing the template DNA samples of the device; and mapping the detection of DNA damage at the map locations to form a mutagen hazard map of the site. More particularly, this aspect includes a method for quantitative mapping of an environmental mutagen hazard site by determining the amount of DNA damage at each map location; and mapping the amount of DNA damage at the map locations to form a quantitative mutagen hazard map of the site.

DNA damage caused by the chemotherapeutic agent cisplatin may be assessed by obtaining a first DNA template sample from a patient subject to cisplatin therapy and reacting a portion of this sample with an amount of cyanide ion displacing cisplatin adducts from the DNA to form a second DNA template. When quantitative polymerase chain reaction amplification is performed utilizing primer sites separated by a least 5,000 base pairs, the cyanide-reacted cisplatin DNA or second DNA template is more amplified than the first DNA template retaining cisplatin. By comparing amplification rates of the first and second DNA templates, DNA damage induced by cisplatin may be assessed. An effective amount of cyanide to displace the cisplatin is about 1 M. The preferred cyanide salt utilized is potassium cyanide and the reaction may be overnight at room temperature. After the overnight incubation of the cyanide-reacted material, any excess cyanide and cisplatin and or cisplatin-cyanide adducts are removed, for example by dialysis. The present invention demonstrates the assessment of DNA damage for a variety of conditions utilizing minute DNA samples, e.g. 1 to 30 ng and preliminary chain reaction primers separated by at least about 5,000 base pairs. Geneotoxin hazard sites may even be mapped by performing the present invention on DNA samples exposed to environmental samples from different locations of the hazard site. In one embodiment a personal DNA geneotoxin exposure dosimeter may be utilized containing two samples of double-stranded DNA templates having DNA primer sites separated by at least 5,000 base pairs. One sample is exposable to the environment and when utilized is exposed to the environment in a manner such that potential geneotoxins may interact with the contained DNA template. One sample is sealed from the environment but carried on the individual to act as a control. After exposure, performance of quantitative long-chain polymerase chain reaction according to the present invention may be utilized to assess DNA damage in the exposed sample. Additionally, certain types of DNA damage may occur which do not inhibit polymerase chain reaction amplifications. The present invention includes methodology to quantitate DNA damage in at least some of those cases, for example, as with the formation of 8-oxo-deoxyguanosine or formamidopyrimidine. This involves converting those damaged sites to DNA strand breaks that do inhibit DNA amplification.

The methods of the present invention may also be used to monitor genetic damage due to self-induced genotoxin exposure such as smoking, sunlight exposure or the aging process. This would, of course, entail control DNA samples for purposes of amplification rate comparisons. Such control samples, for the usual DNA damage inhibiting amplification, require an individual's pre-exposure DNA. A control for DNA damage not inhibiting amplification would be obtained by converting such DNA damae point to, e.g., DNA strand breaks, as mentioned herein for assessing damage relating to 8-oxo-deoxyguanosine of formamidopyrimidine.

While a number of objects and advantages are disclosed above, it is well within the ability of one skilled in the art, in view of the present teachings, to conceive of additional objects and advantages that are still within the scope and spirit of the invention as a whole as disclosed herein.

BRIEF DESCRIPTION OF THE DRAWINGS

FIG. 4. Table of results from Example 2 showing relative amplification product ratio (Rel. Amp) and lesion frequency for increasing length of template.

FIG. 9. Table showing relative amplification product ratio (Rel. Amp) and lesion frequency for increasing length of template and exposure to a DNA damaging agent.

FIG. 11A. in transformed human fibroblasts (■=inactive β-globin; ●=hprt; - -=rate of transcribed strand repair). FIG. 11B. in lymphoblasotid cells from a normal donor GM01989B; GM02344A is from a patient with xeroderma pigmentosum group A; P2 is a lymphoblastoid cell line from a patient with colon cancer a homozygous mutation in a mismatch correction gene, hPMS2; P8 is a lymphoblastoid cell line from a patient with a heterozygous mutation in a mismatch correction gene, hMSH2; P7 is apparently normal lymphoblastoid cell line.

FIG. 12A shows relative amplification as a function of hydrogen peroxide concentration. FIG. 12B shows the lesion frequency.

FIG. 17A and FIG. 17B. Repair kinetics of cisplatin-DNA adduct in human cells. Histograms show relative amplification following a 2 hr 150 μM cisplatin treatment. Solid bar is relative amplification of a nondamaged control. (FIG. 17A=β-globin; FIG. 17B=hprt)

FIG. 18A gives relative amplification and FIG. 18B gives lesions/10 kb.

The drawings are not necessarily to scale and certain features of the invention may be exaggerated in scale or shown in schematic form in the interest of clarity and conciseness. It will be readily apparent to one skilled in the art that various substitutions and modifications may be made to the invention disclosed herein without departing from the scope and spirit of the invention.

DETAILED DESCRIPTION OF THE INVENTION

Figure 1A:
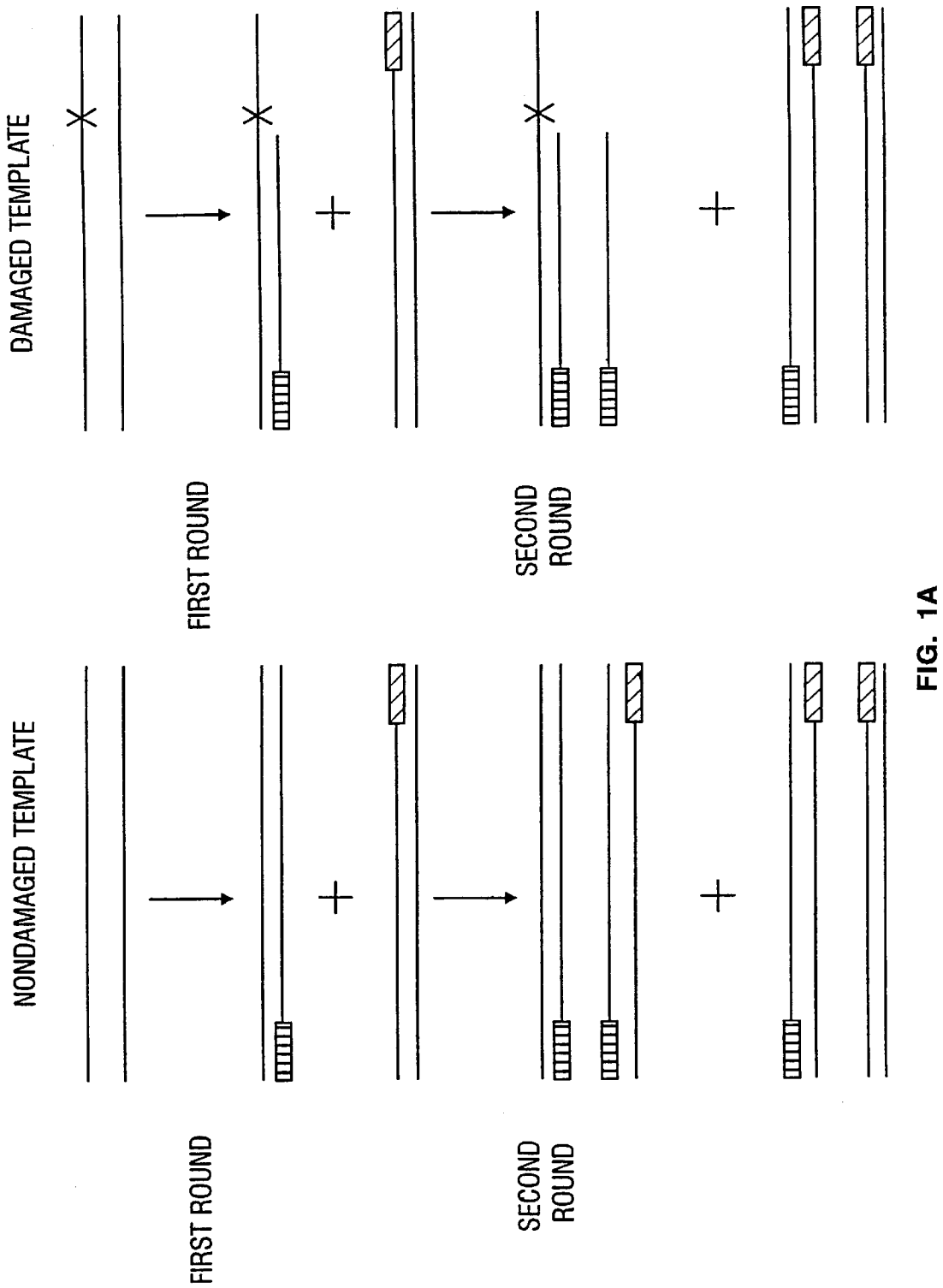
FIG. 1A. Schematic representation of the detection of DNA damage double-stranded DNA in a template sample containing both damaged and undamaged template using quantitative long-DNA amplification.
Figure 1B:
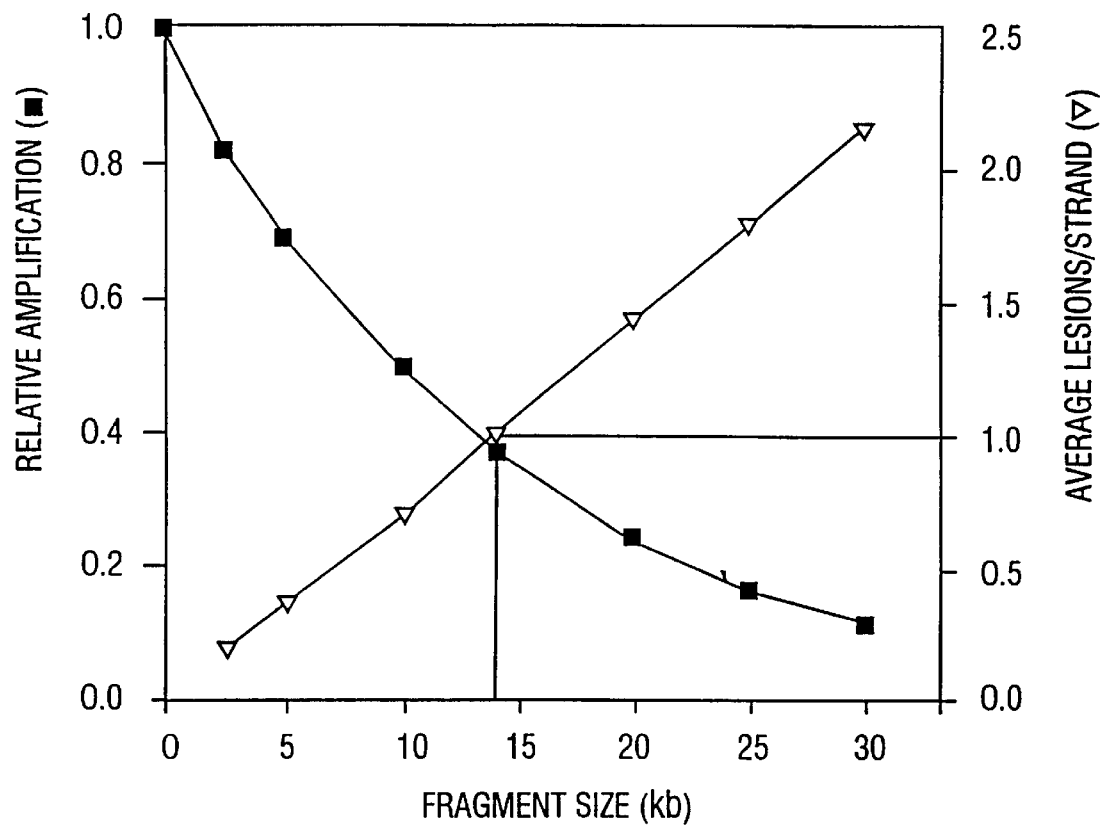
FIG. 1B. Theoretical amplification (left axis) and lesion frequency (right axis) versus fragment size at a fixed amount of DNA damage (Effect of 10 J/m$^2$ of UV light on Amplification).

The present invention includes a method detecting DNA damage in a sample of double-stranded DNA template (see FIG. 1). In the preferred embodiment, the present method uses at least two double-stranded DNA template samples, generally, a control sample and a test sample. The control sample may be a duplicate of the test sample which has not been exposed to DNA damage, or it may be a test sample against which a different test sample is compared. In practice, a test sample of double-stranded DNA template is taken from a system of interest. The system of interest could be an in vitro system, such as cell or tissue culture, or an in vivo system, such as a patient, or an environmental system, such as a chemical spill site. The template is selected such that its individual complementary strands each have a strand-specific primer site, and the primer-sites are separated by at least about 5,000 base pairs in the intact template DNA. Using purified DNA, this method has been used to amplify a 30,000 base pair DNA template. The choice of using purified DNA or not is left to the artisan. For example, from a biological system, chromatin rather than purified DNA may serve the artisan's purpose, whereas, in a chemical system (like a dosimeter) purified DNA template is readily available. If the DNA template used in the method represents a gene-specific DNA sequence, then the method detects gene-specific DNA damage. The amount of double-stranded DNA template necessary in this method is about 50 ηg or less of human genomic DNA (equivalent to about 10,000 cells), with about 5 ηg to about 15 ηg being the low range of starting template DNA.

The template sample or its complementary strands are placed in a proper mixture with an excess of primers to the strand-specific primer-sites. Then quantitative long-DNA amplification is performed on the mixture, to produce amplification products. The amplification products represent substantially only the undamaged individual strands. Any damaged individual strands are substantially not amplified, and therefore comprise negligible amplification product and do not appear in a standard gel analysis.

Typical reactions conditions consist of 50 pmol of each primer, 200 uM dNTPs, 1.5 mM MgCl, 50 mM Tris-Cl, pH 8.0, 2.5 units Ampli-Taq, and 50 μg of purified human cellular DNA in a 50 ul reaction volume. Amplifications may be performed in the Perkin-Elmer 9600 thermocycler which is specially designed for quantitative amplifications. Amplifications are performed by initially denaturing the DNA at 94° C. for 4 minutes, followed by 30 cycles of 94° C., 30 seconds denaturation followed by annealing at 61° C. for 1 minute, and extension at 72° C. for 2 minutes. The final extension step is allowed to continue 7 minutes.

Amplification product is then characterized using any of a number of methods available to one skilled in the art. Such methods include polyacrylamide gel electrophoresis, electrochemiluminescence, radioisotope incorporation and autoradiography and Betascope™ imaging (Betagen, Waltham, Mass.).

The detection of DNA damage in the test sample is accomplished by comparing the results of the characterization of the amplification product of the test sample to the amplification product of a control sample of the same template processed in the same manner as the test sample. If the test sample template yields less amplification product than the control sample, the test sample template DNA sustained damage. If the test sample template and the control sample template yield substantially the same amount of amplification product, the test sample template DNA did not sustain detectable DNA damage. In no case should the test sample template yield more amplification product than the control sample template, as this would indicate a problem with the assay.

The amount of DNA damage in the test sample template may be quantitated by comparing the amount of amplification product from a control template sample against the amount of amplification product from the test sample template. This may be accomplished by using any of a number of methods known to the skilled artisan for quantitating an amount of DNA. These methods include:

A. Gel electrophoresis and radioisotope imaging. Gel electrophoresis is based on the incorporation of dCTP-α-[$^{32}$P] radiolabeled nucleotides into the amplification products during the amplification reaction. The amplification products are then separated from unincorporated dNTPs by electrophoresis in an agarose gel. The agarose gel is then dried and the amount of radioactivity in each band is determined thorough the use of a 2D-radioisotope imaging system such as the Betascope 603 Blot analyzer from Betagen (Waltham, Mass.). This assay is extremely sensitive since the specific activity of the product can be readily adjusted by increasing the amount of radioactive tracer.

B. High Performance Liquid Chromatography. Katz, et al. (Katz et al., 1992), incorporated herein by reference. Amplification products, without any further manipulation, are applied to an anion-exchange column (TSK DEAE-NPR) and eluted with a binary mobile phase of two buffers. A guard column is used in series with the DEAE column to avoid clogging from genomic DNA. The gradient program is dependent upon the specific size of amplification products which are to be resolved. DNA is detected using a UV detector set at 260 nm. The amount of amplification products is determined by previously described standard DNA assays.

C. Electrochemiluminescence (ECL). ECL, is a novel quantitation assay for PCR products which has been developed by Perkin-Elmer. Several different formats have been developed. Here a format was used in which amplification product is tagged on one end with a special electrochemiluminescent probe (TBR) and is tagged on the other end with biotin, through the use of appropriately modified PCR primers. The product is captured using streptavidin coated magnetic beads and the amount of product is quantitated in a special instrument, the QPCR System 5000 (Perkin-Elmer, Norwalk, Conn.), which accurately measures the electrically-stimulated luminescence of the chemical probe.

The ability to amplify large DNA fragments allows for increased sensitivity as shown in FIG. 1A. Recently methods have been reported for the amplification of long PCR fragments (Cheng et al., 1994). Larger DNA fragments will increase the sensitivity as shown in a theoretical plot of the effect of a fixed fluence of UVC light (10 J/m$^2$) on amplification as a function of fragment size, where increasing lesion frequency is shown on the right axis. For example, 10 J/m$^2$ of UVC light produces about 0.2 photoproducts per 2.7 kb and decreases amplification to 80% of a nondamaged control. However, amplification of a 14 kb fragment would be decreased to 37% (one blocking lesion per strand) and amplification of a 30 kb fragment is reduced to around 11% of a nondamaged control.

In another embodiment, the present invention includes a method for determining the rate of DNA repair in a cellular system by taking a sample of a double-stranded DNA template from the system at at least two different times. After processing and quantitating DNA damage in each sample separately, the rate of DNA repair is determined as the change in the amount of amplification product between the samples over the course of time.

This embodiment is useful for diagnosing efficacy of an anti-neoplasia therapy in a patient. Efficacy of an anti-neoplasia therapy may be assessed by monitoring the therapy's effect on the rate of DNA repair in the patient. This is accomplished by taking an initial set of samples of a double-stranded DNA template from the patient and determining a rate of DNA repair as described above. Then, after an appropriate course of time, taking a subsequent set of samples from the patient and again determining a rate of DNA repair. Efficacy of the therapy is diagnosed by comparing the DNA repair rate a the two sampling times. An increasing DNA repair rate, a decreasing DNA repair rate and/or a stable repair rate may be determined using the present method.

Another embodiment of the present invention is a device for detecting the effect of environmental genotoxins. The device comprises at least one double-stranded DNA template sample, to serve as an environmental test sample. One or more additional double-stranded DNA template samples may also be placed in the device to serve as a control sample. The test sample is to be exposed to the environment of interest, but the control sample is not to be so exposed. The test sample template DNA is held in a container which is pervious to the environment or agent in the environment of interest. The control sample is held in a container which is not pervious to the environment or held separate from the environment.

Presence of a genotoxic hazard in an environment may be detected using the device of the present invention. Environmental genotoxins are detected by their effect on the exposed test sample relative to the control sample or some other standard. The test sample will show evidence of DNA damage if a sufficient level of genotoxin is present in the environment to cause DNA damage. This is accomplished by exposing the device to the environment of interest for an effective period of time, processing the template DNA samples of the device to detect DNA damage in the sample template. If the amount of DNA damage in the amplification product is quantitated, then an assessment of the level of risk due to exposure in the environment may be made by comparing the quantity of DNA damage over the period of exposure against a relevant exposure standard or toxicity table.

Additionally, an environmental hazard site may be mapped as to location and risk level of agents effecting DNA damage by placing the instant device at various locations in the environment for an effective period of time, processing the template DNA samples of the devices and quantitating the amount of DNA damage as described herein, and then assessing and plotting the level of risk at each location on a site map. By quantitating the amount of DNA damage at each location, rather than just the presence of a genotoxic effect, a more dynamic understanding of the hazard site can be developed, which is useful in assessing overall risk and planning containment and clean-up priorities for the site.

Further, the instant device may be carried on one's person and use as a personal dosimeter for exposure over time to genotoxic effects.

An effective period of time for exposing the instant device can vary from a very few minutes for ionizing radiation (e.g., radiation therapy) to months for an environmental site assessment. The skilled artisan is able to make an initial assessment of necessary exposure time based on the toxicity, concentration and flux of the agent and other prevailing environmental conditions.

Where it is recited that there are alternative materials and methods are available to one skilled in the art, which alternative the skilled artisan elects will be influenced by the resources available and the degree of familiarity of the artisan with the various alternatives. One skilled in the art in view of this disclosure will be able to practice this invention using equivalent materials and methods of the artisan's own preference.

Tables 1–4 summarize various amplification products, damaging agents, cell lines and repair kinetics demonstrated as used in the following Examples.

TABLE I

Amplification products currently under study

| Gene | size (kb) | Cell origin |
| --- | --- | --- |
| Active | | |
| hprt | 15.4 | human |
| β-polymerase | 12.2 | human |
| β-polymerase | 6.2 | mouse |
| mitochondria | 16.2 | human |
| mitochondria | 16.2 (in development) | mouse |
| p53 | in development | human |
| Inactive | | |
| oxytocin receptor | 14.4 | human |
| β-globin | 17.7 | human |
| β-globin | 8.7 | mouse |

TABLE II

Detection of gene-specific damage using QPCR

| Damaging agent | Comments |
| --- | --- |
| asbestos | generates reactive oxygen species; cause of mesothelioma |
| benzo[a]pyrene diol epoxide | common environmental carcinogen |
| chlorambucil | widely used anti-cancer agent |
| cisplatin | widely used anti-cancer agent |
| glucose oxidase | produces hydrogen peroxide |
| hydrogen peroxide ($H_2O_2$) | reactive oxygen species |
| paraquat | common herbicide; generates reactive oxygen species |
| TPZ (tirapazamine) | increases the effectiveness of cisplatin |
| UV | cause of skin cancer |

TABLE III

Cell lines examined by QPCR

| Cells | Organism | Damaging agent |
| --- | --- | --- |
| transformed fibroblasts | human | UV[a], BPDE[b], cisplatin, oxidants[c] |
| transformed epithelial cells | human | chlorambucil |
| transformed mesothelial | human | asbestos |
| lymphoblastoid | human | UV |
| primary lymphocytes | human | UV, TNF-α |
| primary endothelial | human | hydrogen peroxide |
| transformed endothelial | human | chlorambucil |
| neutrophils | mouse | LPS[d] | a, UV = ultraviolet light, 254 nm
b, BPDE = benzo[a]pyrene diol epoxide
c, oxidants = hydrogen peroxide, glucose oxidase, paraquat, TPZ (tirapazamine)
d, LPS = lipopolysaccharide

TABLE IV

Repair Kinetics of Human Cells Studied by QPCR.

| Mutant | Cell type | Damaging Agent | Comments |
| --- | --- | --- | --- |
| WT | transformed fibroblast | UV | • rapid repair intranscribed gene |
| | | BPDE | • transcribed gene damaged more |
| | | cisplatin | • repaired slower than UV |
| | | $H_2O_2$ glucose oxidase | each agent causes more mt DNA which is poorly repaired |
| WT | transformed mesothelial cells | asbestos | |
| WT | lymphoblastoid | UV | • rapid repair |
| WT | primary lymphocytes | UV | |
| WT | smooth muscle | $H_2O_2$ | |
| WT | primary umbical vein | $H_2O_2$ | |

TABLE IV-continued

Repair Kinetics of Human Cells Studied by QPCR.

| Mutant | Cell type | Damaging Agent | Comments |
|---|---|---|---|
| WT | endothelial cell | $H_2O_2$ | |
| XPA | fibroblast | UV | • repair deficient |
| XPA | lymphoblastoid | UV | • repair deficient |
| XPC | lymphoblastoid | UV | • slow repair in non-transcribed genes |
| PMS2⁻ (P2) | lymphoblastoid | UV | • slow repair |
| PMS2⁺/⁻ (P7) | lymphoblastoid | UV | • slow repair |

The following examples are intended as illustrations of the practice of this invention and are not meant to limit the scope of the invention.

EXAMPLE 1

Isolation and Digestion of Genomic DNA

Isolation of genomic DNA.

Lysis buffer (2% SDS, 0.5 M NaCl, 0.05 M EDTA, 50 mM Tris-HCl, pH 7.5) containing 200 ug/ml proteinase K was added to thawed cell pellets (3.0 ml/1–5×10⁶ cells) and was incubated overnight at 37° C. The lysates were extracted twice with PCI, and once with CI. The top aqueous phase was removed to an autoclaved 15 ml Corex tube and 1/10 volume of 3 M sodium acetate and 2.5 volumes cold 100% ethanol were added. The DNA was precipitated at −20° C. for >30 minutes, and then collected by centrifugation at 4° C. for 30 minutes at 8,000 rpm. Pellets were rinsed in 70% ethanol, dried in air, and resuspended in TE buffer.

Digestion of genomic DNA.

DNA was incubated with 3–5 Units/ug DNA of BamHI overnight at 37° C., followed by 2 PCI and 1 CI extraction. DNA was then precipitated in 2.5 volumes of 100% ethanol, washed with 70% ethanol, and resuspended in TE buffer. DNA concentration was quantitated by fluorometry using Hoechst dye 33258.

EXAMPLE 2

Amplification of Long-DNA Templates

Figure 2:
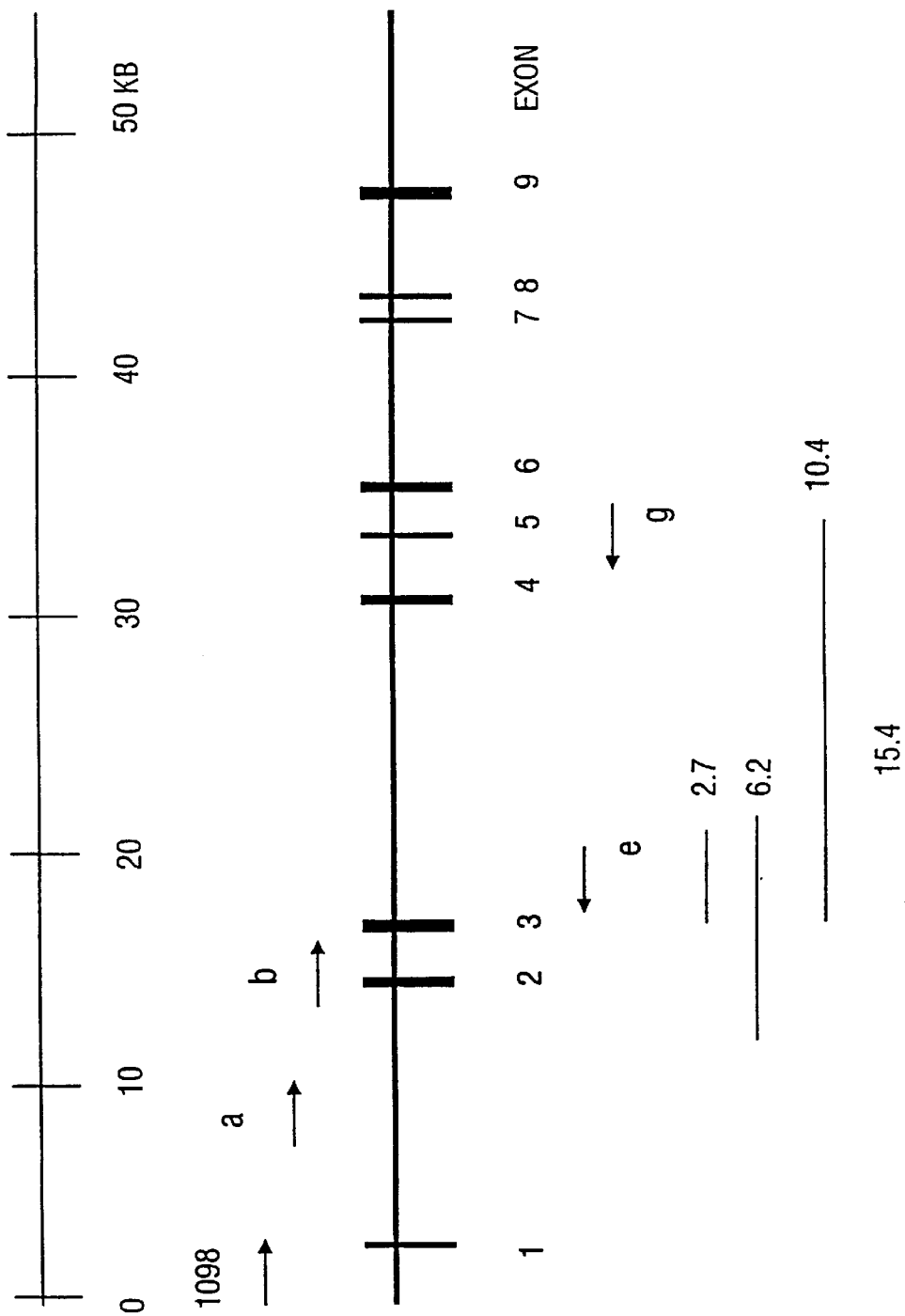
FIG. 2. Long-DNA amplification fragments from the human hypoxanthine phosphoribosyltransferase gene locus (hprt).

Previously, the longest DNA template amplified using PCR is reported as a 2.7 kb fragment of the hprt gene from oligonucleotide b to e (see FIG. 2). The present example describes the quantitative long-DNA amplification of 2.7 kb, 6.2 kb, 10.4 kb, and 15.4 kb DNA fragments from hprt locus (FIG. 2), and 17.7 and 24 kb fragments from the β-globin gene and the entire 16.2 kb human mitochondria genome. These amplifications were accomplished using XLPCR™ conditions (Perkin Elmer/Roche).

Figure 3:
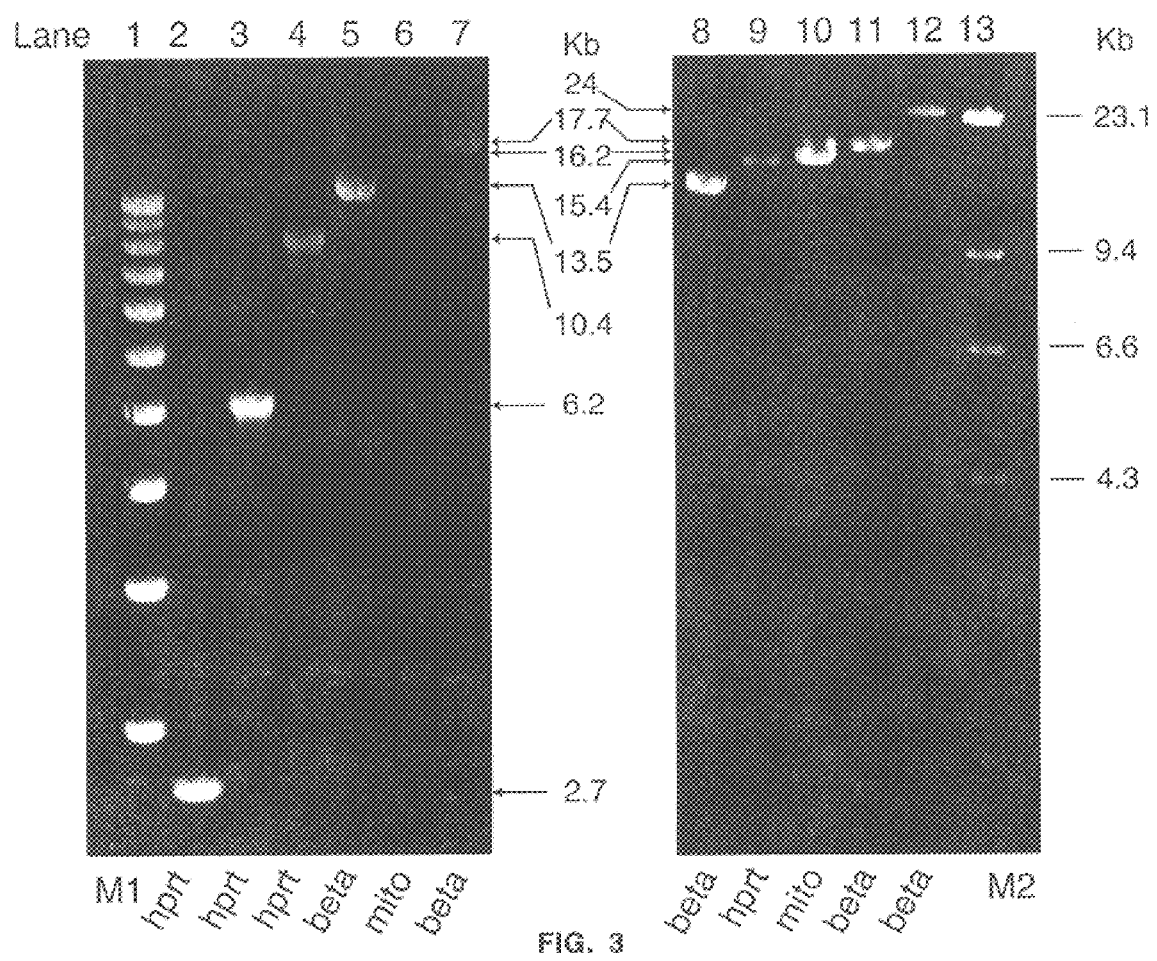
FIG. 3. Amplification of long-DNA templates: from the human hprt gene the 2.7 kb, 6.2 kb, 10.4 kb, and 15.4 kb fragments in lanes 2–4 and 9 respectively; from the β-globin gene the 13.5 kb fragment in lanes 5 & 8, the 17.7 kb fragment in lanes 7 & 11 and the 24 kb fragment in lane 12; and the entire 16.2 kb human mitochondrial genome in lanes 6 & 10. M1 is a 1 KB ladder standard and M2 is a λ-phage/Hind III standard.

FIG. 3 is a photograph of ethidium bromide stained agarose gels in which 50 ng of genomic DNA was amplified using various primer sets and special XLPCR™ reagents and conditions. Specifically, 50 ng of DNA was added to a reaction mixture containing dNTPs (200 µM), glycerol (8%), DMSO (2%), Tricene-acetate (25 mM, pH 8.0), potassium acetate (25 mM), magnesium acetate (1 mM), and 10 pmol each primer. After prewarming to 75° C. for 90 seconds a combination of thermostable polymerases (rTth, 1 unit, and Vent with rTth>>Vent) were added. After a 94° C. 1 minute denaturation the reactions were subjected to 36 cycles of 94° C., 15 sec, 68° C. for 12 minutes. A 10 µL aliquot of each reaction mixture was loaded on to a 0.6% agarose gel (Bethesda Research Labs) for lanes 1 to 7, or a 0.4% SeaKem™ agarose gel for lanes 8 to 13. Gels were electrophoresed at 100 V/13 cm for 4 hours.

FIG. 3 shows amplification of long-DNA templates: from the human hprt gene the 2.7 kb, 6.2 kb, 10.4 kb, and 15.4 kb fragments in lanes 2–4 and 9 respectively; from the β-globin gene the 13.5 kb fragment in lanes 5 & 8, the 17.7 kb fragment in lanes 7 & 11 and the 24 kb fragment in lane 12; and the entire 16.2 kb human mitochondrial genome in lanes 6 & 10. M1 is a 1 KB ladder standard and M2 is a λ-phage/Hind III standard. The results of this example are given in the table of FIG. 4.

EXAMPLE 3

Quantitative Amplification of Long-DNA Templates

Figure 7:
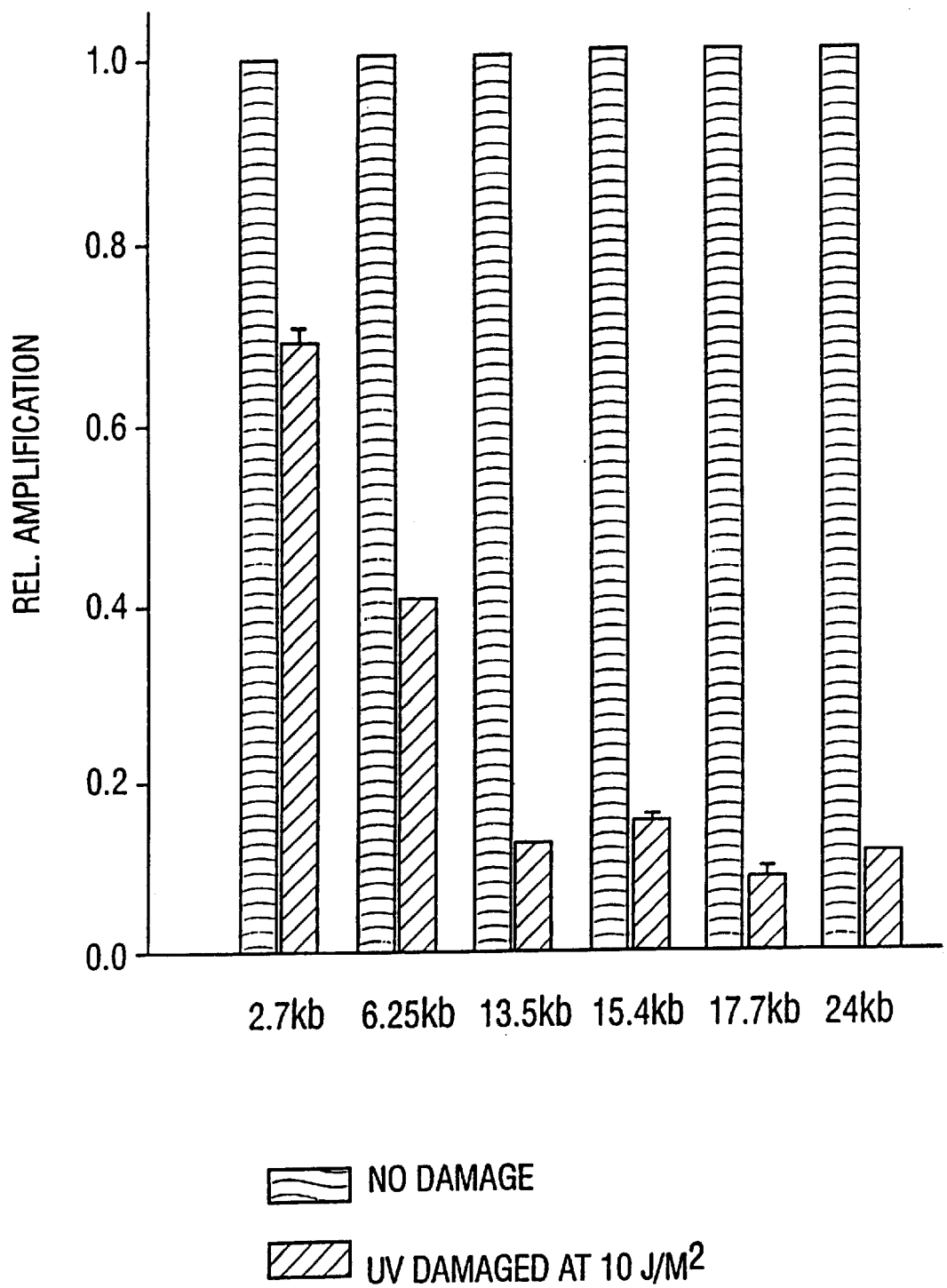
FIG. 7. Effects of 10 J/m$^2$ UV light on the relative amplification of various sizes of DNA template. Error bars for the 2.7 kb, 15.4 kb, and 17.7 kb templates is the mean ±S.E. of three separate long-DNA amplifications reactions quantified two-times for each reaction (total n=6).
Figure 8A:
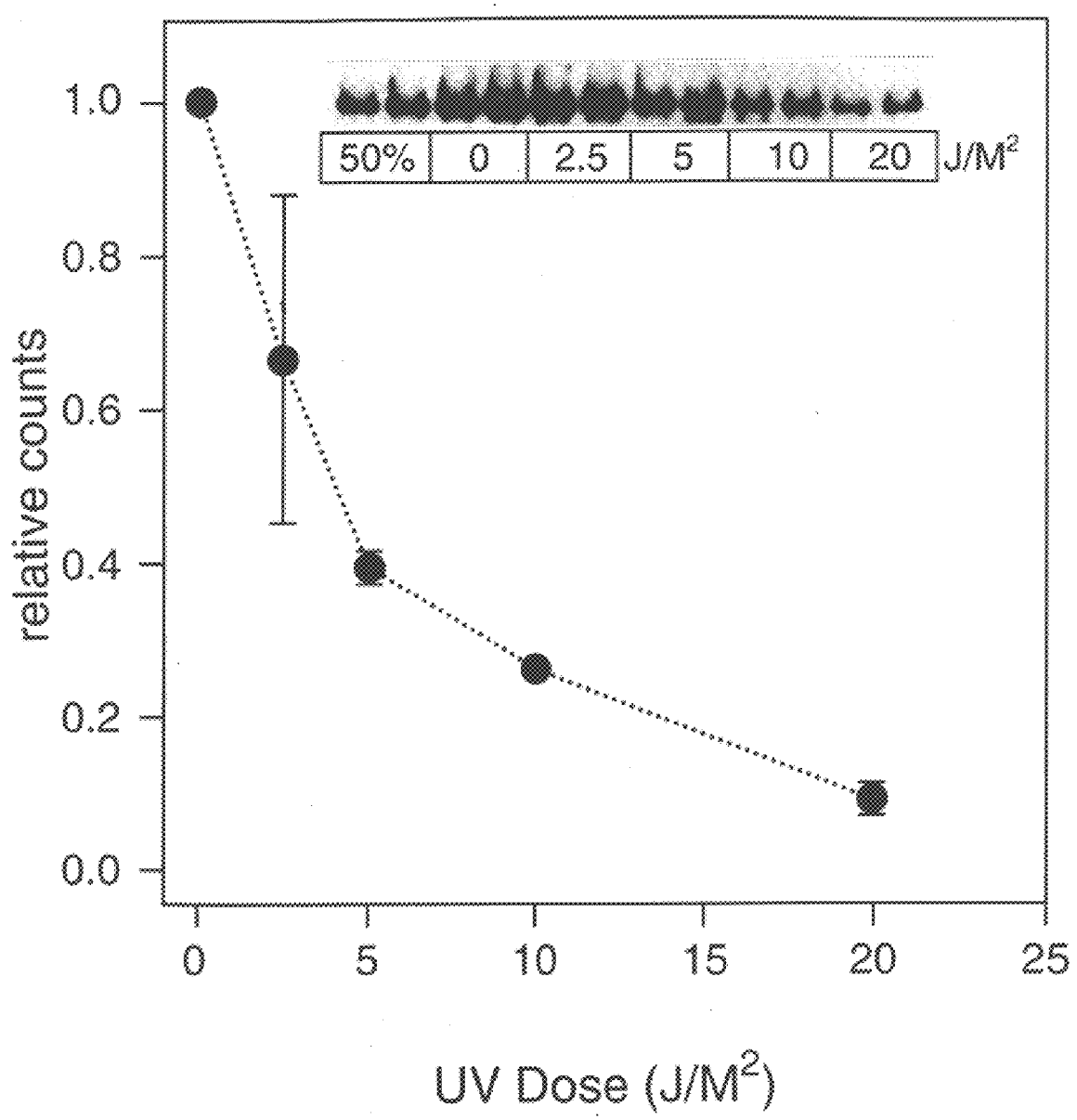
FIG. 8A and FIG. 8B. Effects of UV light on the relative amplification of 15.4 kb hprt human genomic DNA template (FIG. 8A) and resulting lesion frequency (FIG. 8B).
Figure 8B:
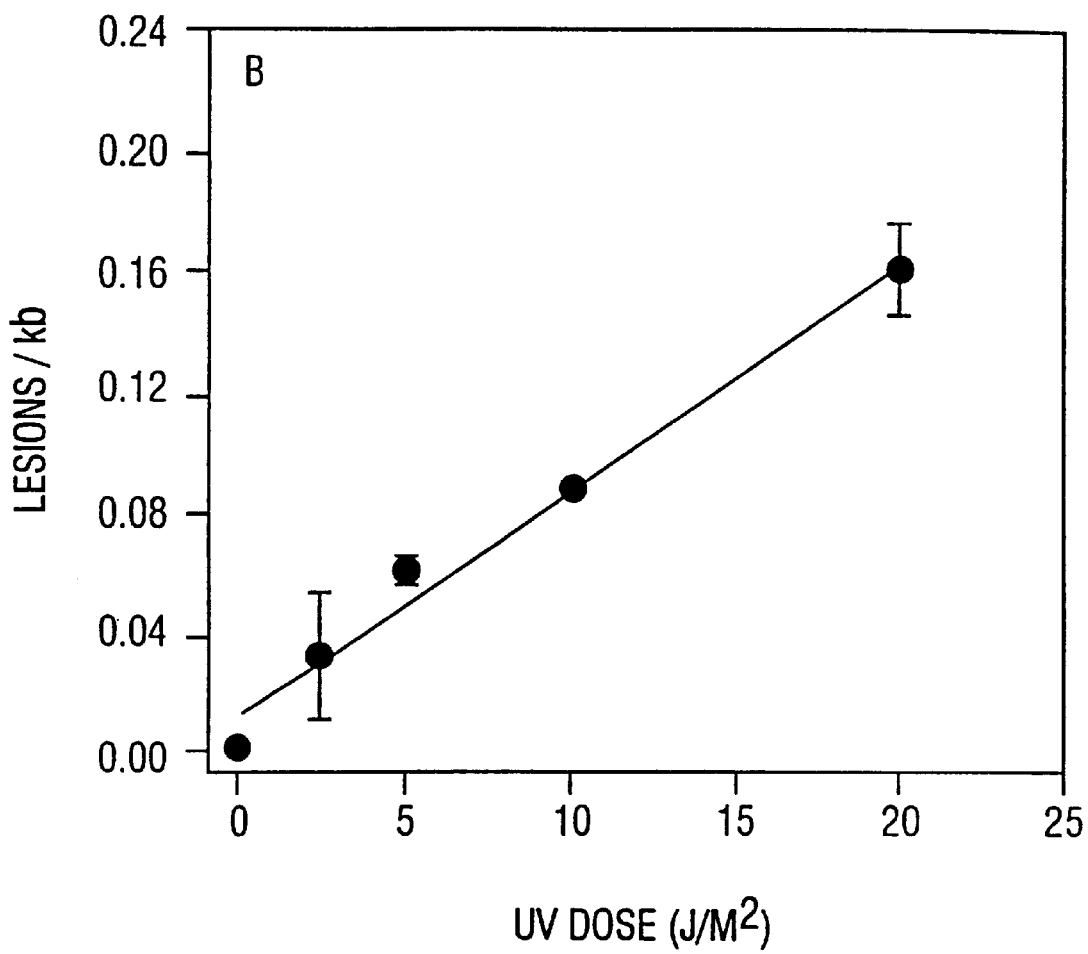
Figure 8C:
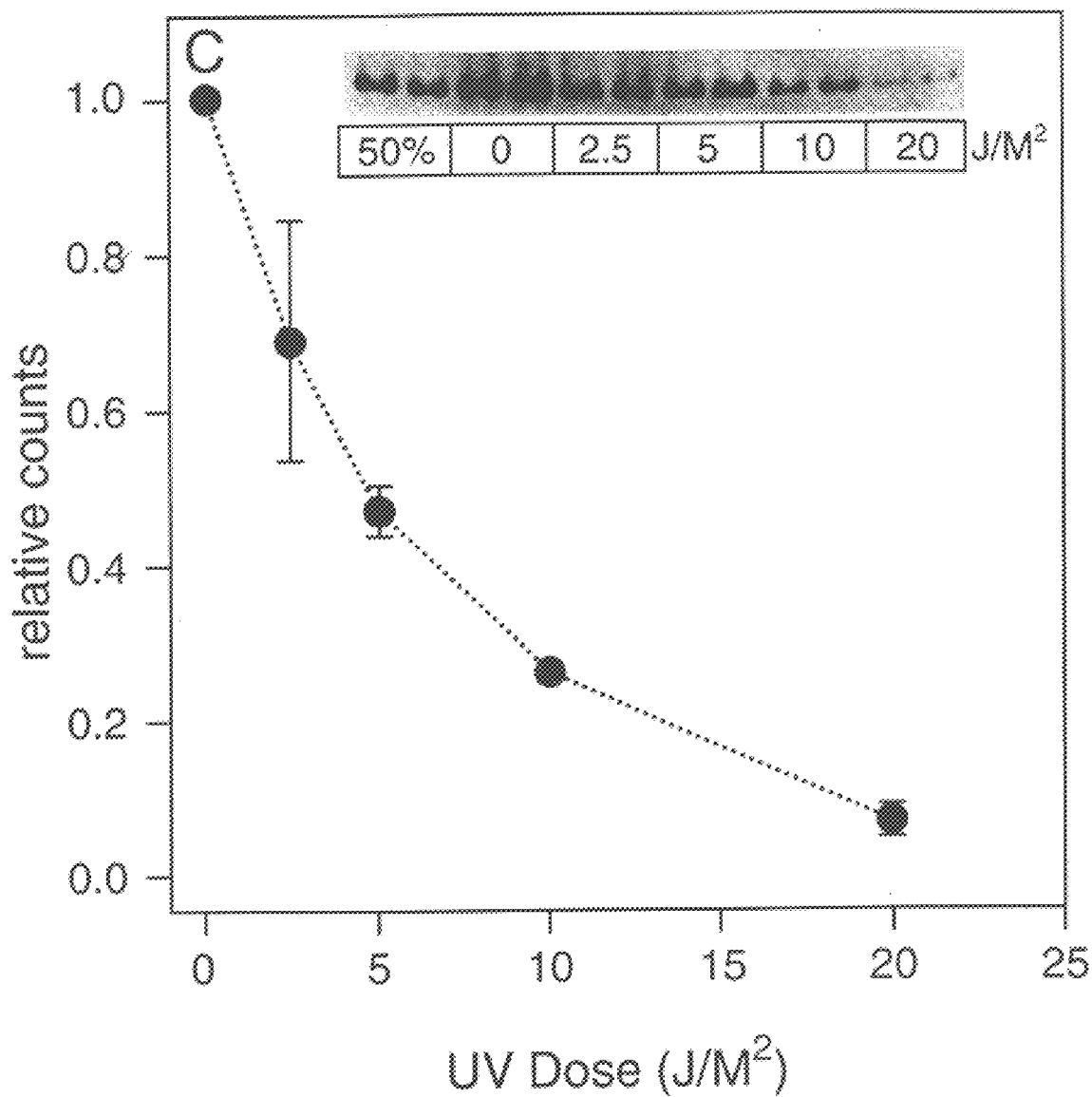
FIG. 8C and FIG. 8D. Effects of UV light on the relative amplification (FIG. 8C) of a 17.7 β-globin kb human genomic DNA template, and resulting lesion frequency (FIG. 8D).
Figure 8D:
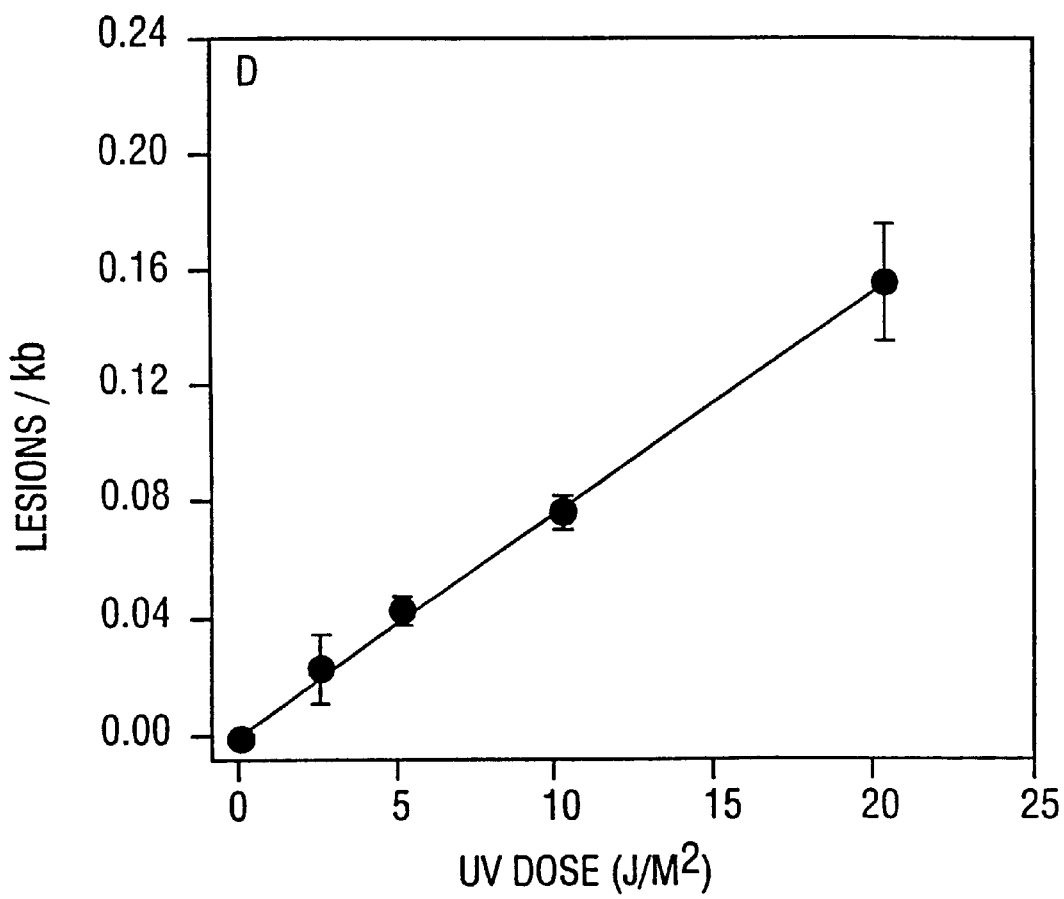

Quantitative long-DNA amplification conditions, i.e., conditions in which the amount of amplification is directly proportional to the amount of added template, were determined by examining the amount of amplification product at various cycles of the amplification reaction at different amounts of added template. The results of this determination for the quantitative conditions used for amplification of the 15.4 kb hprt fragment and the 17.7 kb β-globin fragment are shown in FIG. 7.

Figure 5A:
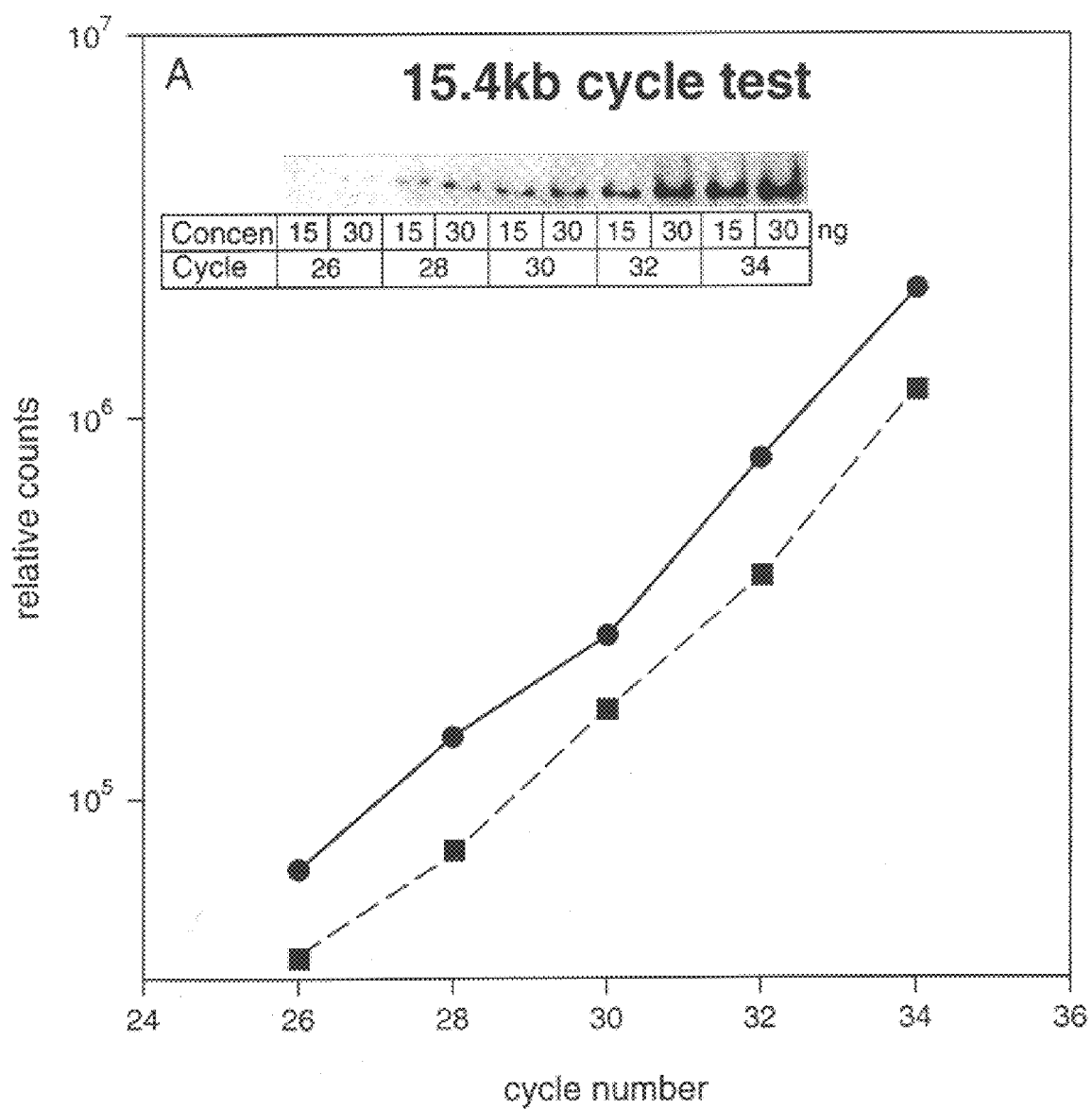
FIG. 5A. The effect of cycle number on the amount of amplification product for 15.4 kb human hprt fragment.
Figure 5B:
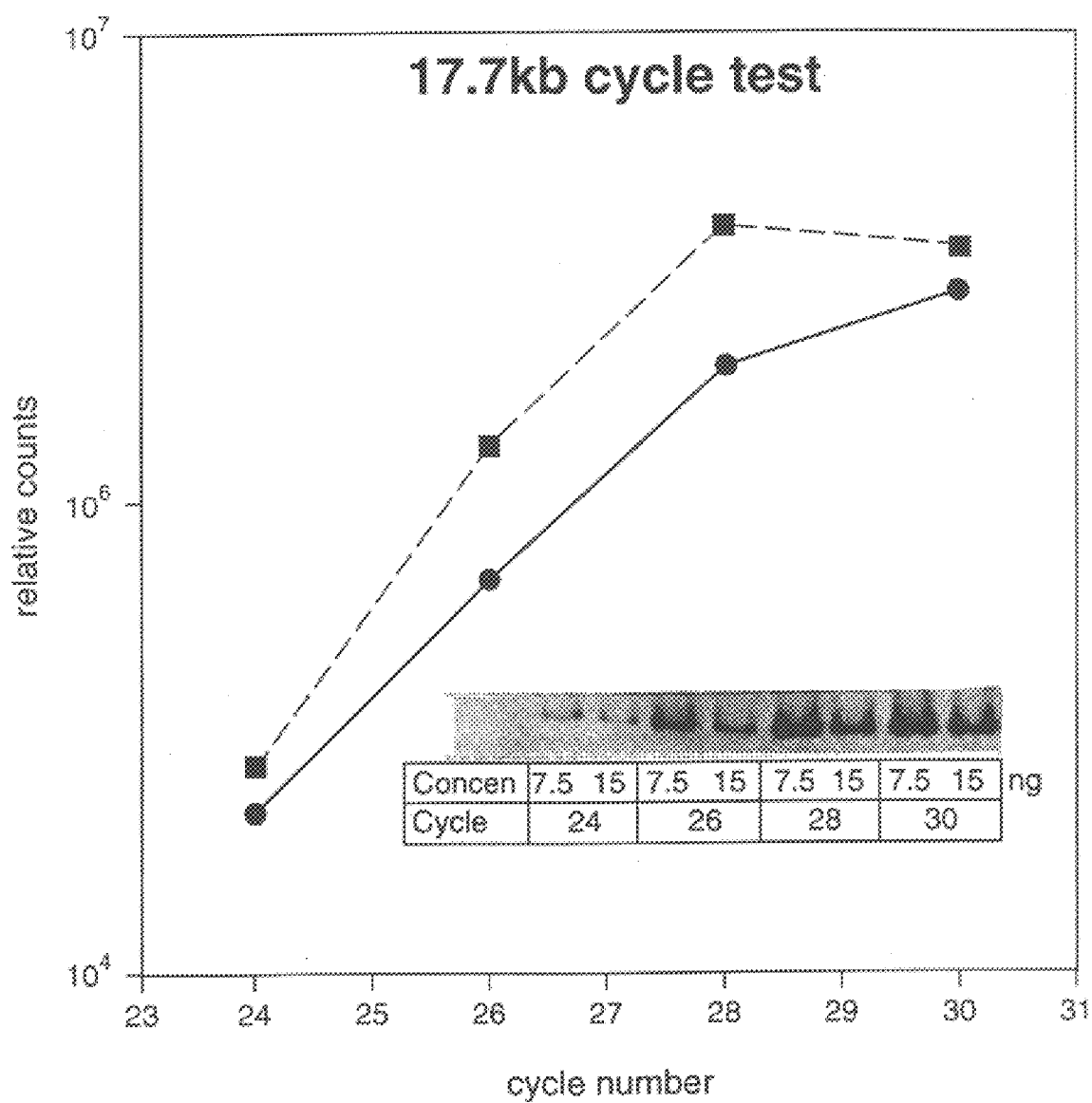
FIG. 5B. The effect of cycle number on the amount of amplification product for 17.7 kb β-globin fragment.
Figure 5C:
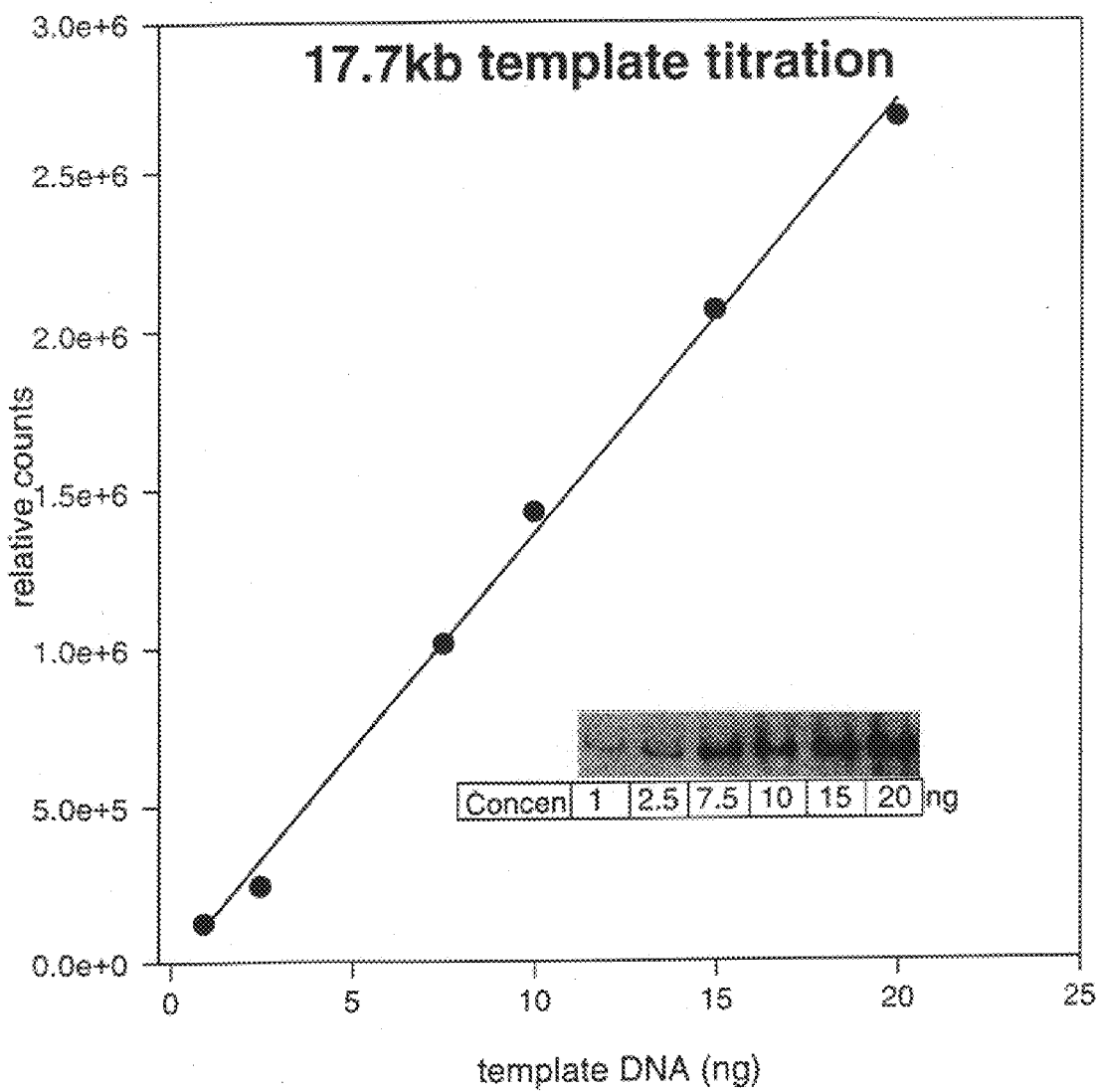
FIG. 5C. The relative amplification of the 17.7 kb fragment at 27 cycles as a function of template concentration from 0–30 ng.

FIG. 5A shows the effect of cycle number on the amount of amplification for the 15.4 kb human hprt fragment. FIG. 5B shows the effect of cycle number on the amount of amplification for the 17.7 kb β-globin fragment. FIG. 5C shows the relative amplification of the 17.7 kb fragment at 27 cycles as a function of template concentration from 0–30 ng.

EXAMPLE 4

Detecting and Quantitating Long-DNA Template Damage

Figure 6:
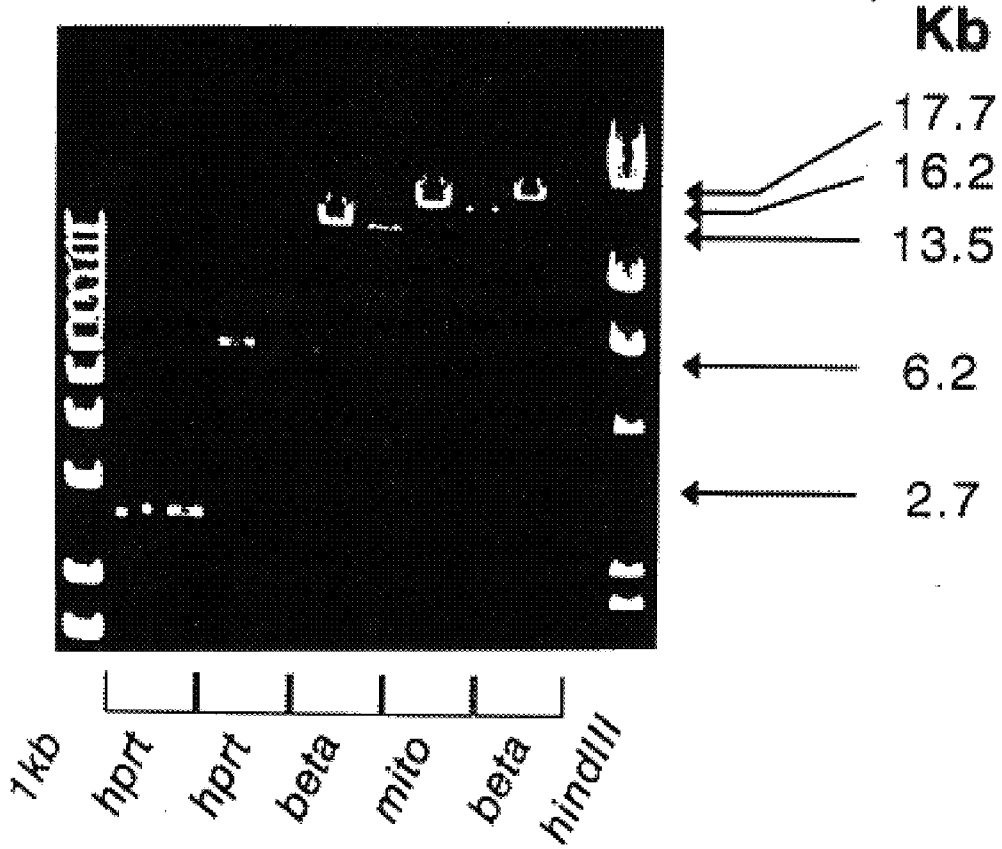
FIG. 6. Ethidium bromide stained gel of amplification products generated from UV-damaged human genomic template (irradiated with 10 J/m$^2$ of UVC) and nondamaged genomic DNA in the practice of the present invention.

Various length template test samples of purified human genomic DNA were irradiated with 10 J/m² of UVC light to cause damage to the DNA. These irradiated template test samples and corresponding nonirradiated template control samples were processed according to the practice of the present invention. Amplification products were radiolabeled by the incorporation of [α-³²P]-dATP during the amplification process. The amplification products for each sample were characterized using agarose gel electrophoresis, ethidum bromide staining and autoradiography (see FIG. 6). DNA damage in the test sample template was detected as lesser intensity of ethidium bromide staining of amplification products from the test sample relative to the control sample. In FIG. 6, quantification of DNA damage was determined by radioisotope imaging using a PhosphorImager™ and Image Quant™ (Molecular Dynamics) software.

Substantially, only the nondamaged templates in a sample will participate in the quantitative amplification reaction. Therefore, this assay is a general measure the fraction of template molecules which contain no damage. This is accomplished by quantifying the amount of amplification product ($A_D$) from test sample and dividing it by the amount of amplification product ($A_o$) from an equal amount of untreated control sample. Assuming a random distribution of lesions, and using the Poisson equation $$f(x)=e^{-\lambda}\lambda^x/x!$$

for the zero class molecules (i.e., those containing no damage), $f(0)=e^{-\lambda}$, where λ=average lesion frequency, the lesion frequency per genomic strand can be calculated: $\lambda = -\ln A_D/A_O$. Therefore, the assay measures the average lesion frequency per strand for the two template strands in the genomic segment of interest.

Using the Poisson expression of the zero class the lesion frequency (L) was determined per DNA fragment as $L = -\ln A_{UV}/A_O$, where $A_{UV}$=the amount of amplification following UV damage and $A_O$ is the amount of amplification of the nondamage control. In order to compare the relative error associated with each fragment size, the amount of damage was normalized to one kb by dividing each fragment by its total length.

The relative amplification product was determined for various length templates and is displayed in FIG. 7. As can be seen this dose of UV while decreasing the amplification of the 2.7 kb fragment only 30% decreased the amplification of the 15.4 hprt and 17.7 globin fragment 85% and 92% respectively. These data followed the hypothetical plot shown in FIG. 4, and clearly demonstrated the utility of long-DNA templates for increased sensitivity to detect and quantitate DNA damage.

EXAMPLE 5

Reproducability

Dose-response curves were generated to establish the reproducibility of the gene-specific assay and the lowest detectable UV dose to human cells (FIG. 10) using DNA extracts from cells which had been exposed to various doses of UV light. Quadruplicate sets of culture dishes plated with human cells were treated with 0, 2.5, 5, 10, and 20 J/m² of UV light at 254 nanometers. The DNA was harvested immediately and used in two separate quantitative long-DNA amplification reactions. Each amplification reaction was analyzed twice. The points represent the mean of n=16 +/−S.D. determinations. The amount of template DNA damage was determined from the relative decrease in amplification product as described above. As in FIGS. 8A–D, the damage resulting from 2.5 J/m² of UV light was easily detected (see table, FIG. 9). Furthermore the precision at which the damage was detected is 5–10% CV. These results demonstrated predictable dose-response with high precision at low doses.

EXAMPLE 6

Determination of DNA Repair in Actively Growing Human Cells

Figure 10:
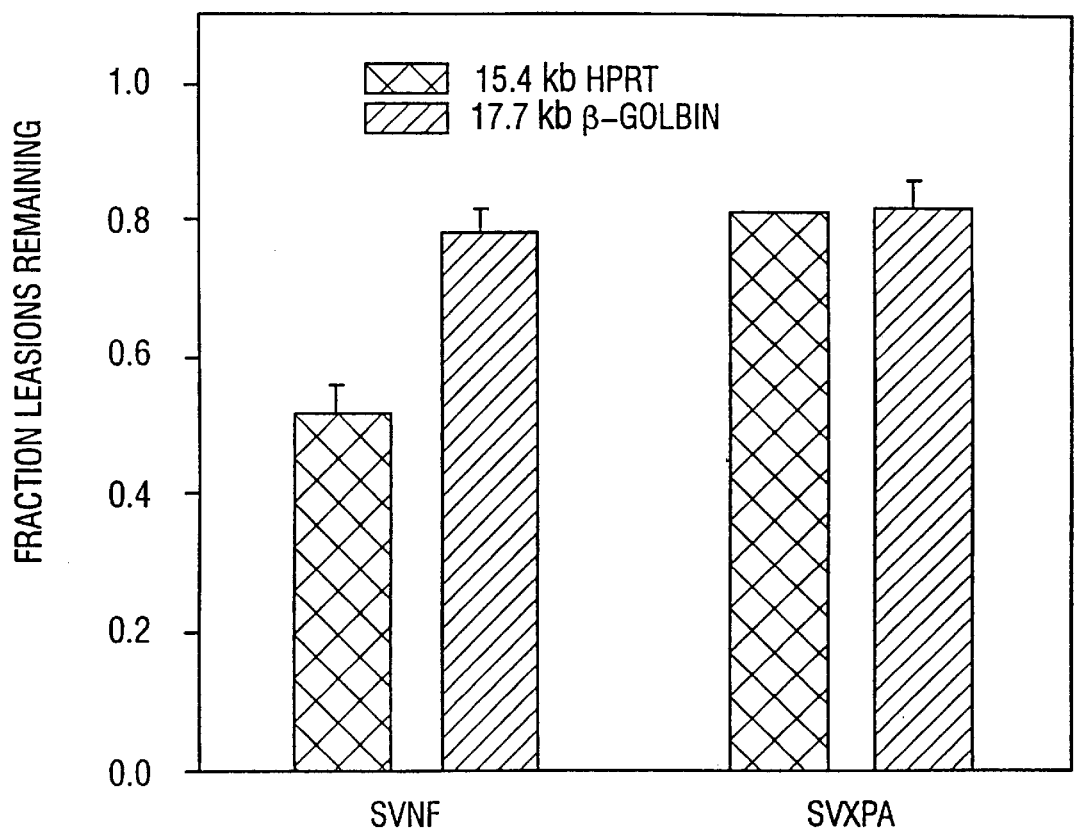
FIG. 10. UV Repair kinetics in normal cells and repair deficient (XPA) cells.

Template DNA form the active hprt gene and the inactive β-globin gene was used in the long-DNA amplification assay to determine DNA repair in actively growing human cells. DNA repair deficient xeroderma pigmentosum (group A) cells were used as an external control for comparison. Quadruplicate plates of normal human cells or repair deficient cells from a patient with xeroderma pigmentosum (group A) were treated with 10 J/m² of UV light and harvested immediately or allowed 8 hours for repair. For normal cells the DNA was harvested and used in two separate long-DNA amplification reactions. Amplification product from each amplification reaction was analyzed twice. The results of this analysis are shown in FIG. 10, where the points represent the mean of n=16 ±S.D. determinations for normal cells. XPA data represent the mean of one long-DNA amplification reaction from four separate DNA samples. FIG. 10 demonstrates that in normal cells there was significant repair in the active hprt gene, but little or no repair in the inactive β-globin gene. Further, there was little or no repair observed for either of these two genes in repair deficient XPA cells.

Having determined DNA damage in a system at two different times, the rate of DNA repair was determined as the relative difference in the amount of amplification product at the two times over the difference in time.

Repair kinetics in different mutant cell lines. In order to validate the use of this novel QPCR assay the repair kinetics of UV-induced DNA damage in a 15.4 kb fragment from the expressed human hprt gene and a 17.7 kb fragment from the non-expressed β-globin gene from several different human cell lines were characterized. Human cells were treated with UV light (10 J/m²). The DNA was extracted using QIAamp® Tissue Kit (QIAGEN, Inc, Chatsworth, Calif.). In this approach the DNA is extracted from cells without the use of harsh organic compounds which can induce significant amounts of oxidative DNA damage. Briefly the frozen cell pellet is lysed in a chaotropic buffer supplied by the manufacturer which contains Proteinase K. The DNA is precipitated and loaded on to a spin column. The DNA is eluted in a TE buffer (10 mM Tris-Cl, 1 mM EDTA). The DNA is diluted and its precise concentration is determined by ethidium bromide fluorescence. These DNA are used in the QPCR assay. Long fragments were amplified using a XLPCR kit from Perkin-Elmer and rTth thermostable enzyme supplied with the kit. [$P^{32}$]-α-dATP was added to each reaction as a tracer and the radiolabeled fragments are separated on 0.6% vertical agarose gels. Radiolabeled amplification products were quantified from dried agarose gels using a Phosphor Imager 425 and ImageQuant™ software (Molecular Dynamics). Lesion frequencies were calculated by quantifying the amount of amplification ($A_D$) from genotoxin-treated sample and dividing it by the amount of amplification ($A_O$) from an equal amount of untreated control sample. Assuming a random distribution of lesions, and using the Poisson equation $$[f(x)=e^{-\lambda}\lambda^x/x!]$$

for the zero class molecules (ie, those containing no damage), $f(0)=e^{-\lambda}$, where $\lambda$=average lesion frequency, the lesion frequency per genomic strand can be calculated as, $\lambda = -\ln A_D/A_O$.

Figure 11A:
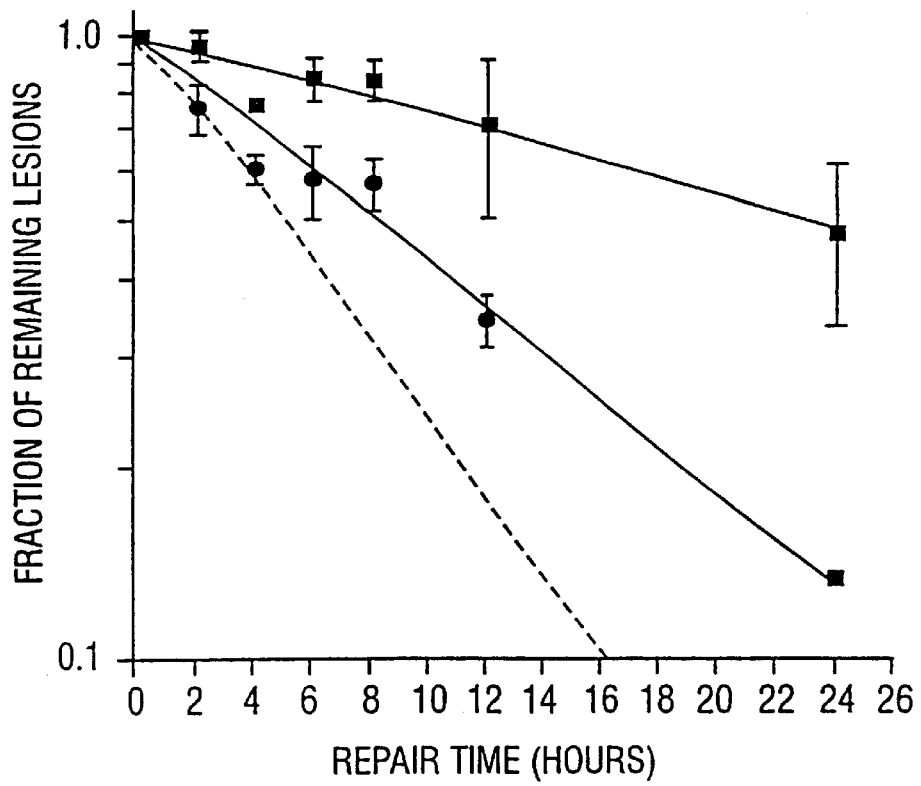
FIGS. 11A and 11B. DNA repair kinetics.
Figure 11B:
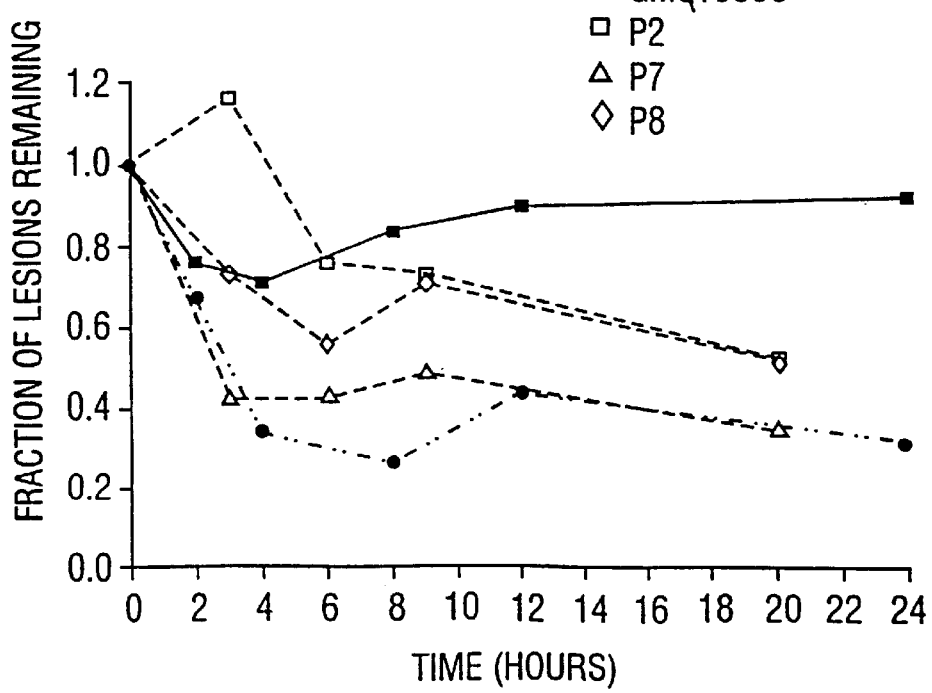

Repair of UV-induced photoproducts following 10 J/m² in an SV40- transformed fibroblast is shown in FIG. 11A for both the expressed hprt gene (●) and the non-expressed β-globin gene (■) where each data point is the N=4 ±SEM. These data clearly show that the non-expressed β-globin gene ($t_{1/2}$=23.5) is repaired significantly slower than the hprt gene ($t_{1/2}$=8.3 hr). The dashed line is the calculated rate of repair for the actively transcribed strand of the hprt gene ($t_{1/2}$=5.0 hr). Repair kinetics have also been performed in several adenovirus transformed human lymphoblastoid cell lines. These include: GM01989B is apparently normal; GM02344A is from a patient with xeroderma pigmentosum group A; P2 is a lymphoblastoid cell line from a patient with a homozygous mutation in a mismatch correction gene, hPMS2; P8 is a lymphoblastoid cell line from a patient with a heterozygous mutation in a mismatch correction gene, hMSH2; P7 is apparently normal lymphoblastoid cell line. P2, P7, and P8 were obtained in collaboration with Dr. Isabel Mellon (University of Kentucky) who is examining the repair kinetics of these cell lines using the pyrimidine dimer specific gene-specific assay. The results presented in FIG. 11B show clear differences in gene-specific repair among several individuals and also among different cell types (For simplicity only repair in the β-globin gene is shown, FIG.

11B). Note that repair in the fibroblast cell line is slower as compared to the lymphoblastoid cell line (GM019889B). The XPA line (GM02344A) shows the slowest repair kinetics and is consistent with published information on XPA cell lines. Also note that repair in P7 is faster than the mismatch defective line P2. These results are consistent with unpublished gene-specific repair kinetics from Dr. Mellon's laboratory.

EXAMPLE 7

Multiplex DNA Damage Detection Simultaneous Analysis of DNA Damage in More Than One Template For multiplex quantitative long-DNA amplification, samples contained 30–60 ng of DNA incubated in GeneAmp PCR buffer II (50 mM KCl, 10 mM Tris-HCl, pH 8.3), 1.5 mM $MgCl_2$, 200 uM each dNTP, 2 uCi dCTP-α-[$^{32}$P], 0.05 to 1.0 uM of each primer, and 2.5 U AmpliTaq DNA Polymerase (Perkin-Elmer) in a 50 ul reaction volume. In a Perkin-Elmer GeneAmp PCR System 9600 thermocycler, the samples were denatured at 94° for 4 min and underwent 13 cycles of denaturation at 94° for 15 sec, with a 40 sec ramp to primer annealing at 48° for 30 sec, and extension at 72° for 2 min, before a final 7 min extension at 72°. Following the amplification reaction, the samples were run on 1% vertical agarose gel, dried, and quantified by Betascope radioisotope imaging (see FIG. 3).

In this example, the concentration of the two primer sets have been titrated so that approximately equal amounts of amplification products were produced from each template sample. We have found that amplification of one product influences the amplification of the other product in a multiplex amplification reaction. Therefore, the relative amounts of the two primer sets were worked out empirically to produce equal amounts of each amplification product.

In a multiplex amplification reaction, to ensure that the selected primers produce the desired size products in a quantitative manner it is essential that two important parameters, template concentration and number of PCR cycles, be examined prior to any damage quantitation studies. The synthesis of the amplification product is ultimately linked to the amount of template and the number of amplification cycles. Amplification goes through three discrete phases: 1) the product increases exponentially with cycle number, 2) the product increases arithmetically with cycle number, and 3) the product begins to approach the amount of primers, and the product will not increase or will actually decline with increased cycles. Hence, more cycles is not necessarily better for quantitative long-DNA amplification since it is essential that the amount of product is proportional to the amount of template. Therefore, all quantitative long-DNA amplifications must be performed under conditions where product concentration increases in a known manner. Generally, after 18 cycles of amplification, twice the amount of template does not yield twice the amount of product for each gene.

For gene-specific assay it is essential that the amount of amplification product increases exponentially with increasing cycles and that the amount of amplification product is dependent upon the template concentration. Therefore, it is preferred that the amplification reactions run for about 13 PCR cycles (Van Houten et al., 1993).

EXAMPLE 8

Detection of Oxidative DNA Damage in Human Cells

Figure 12A:
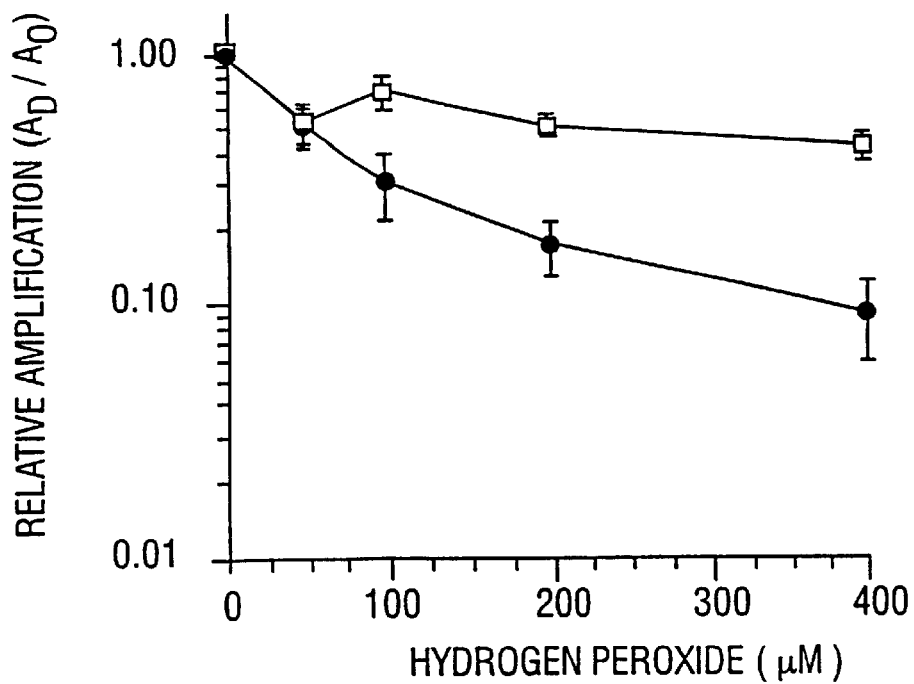
FIGS. 12A and 12B. Formation of hydrogen peroxide-induced DNA damage in mitochondrial DNA and a nuclear gene from human fibroblasts.
Figure 12B:
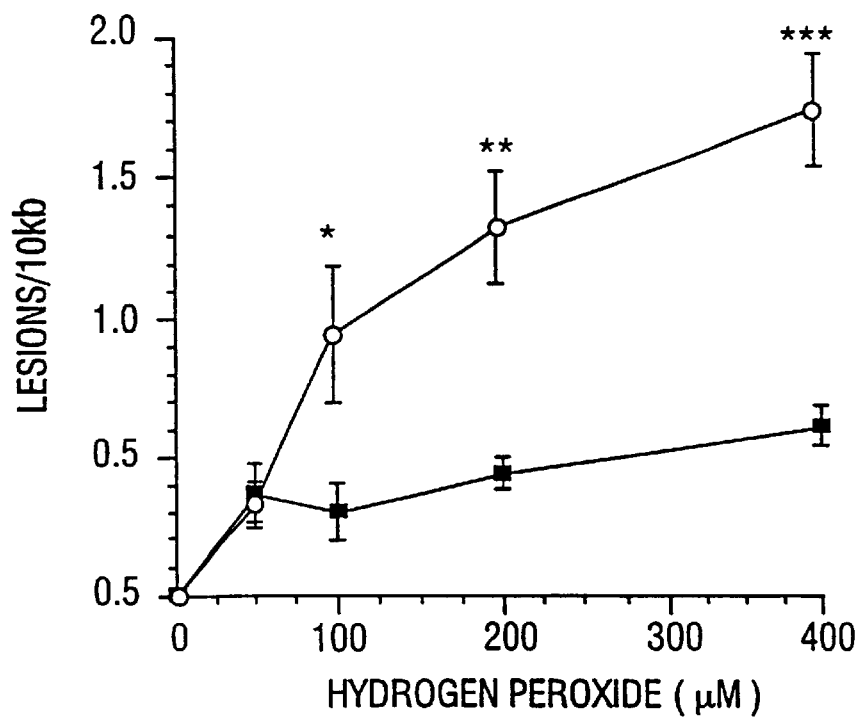

Formation and repair of oxidative DNA damage in the nucleus and mitochondria of human fibroblasts after hydrogen peroxide. Reactive oxygen species (ROS) are produced by a wide variety of physical and chemical agents, and can also arise endogenously via leakage of oxygen from the electron transport in the mitochondria and from other cellular biochemical processes. Whether DNA damage by ROS occurs heterogeneously throughout the human genome, and whether this damage is repaired, were examined. Human SV40-transformed fibroblasts (SVNF) were treated with 0–400 uM $H_2O_2$ for 1 hour. The DNA was extracted using a QIAGEN columns and used for amplification of a 16.2 kb mitochondrial gene fragment (●) and 17.7 kb β-globin gene fragment (■) (FIGS. 12A and 12B). FIG. 12A shows the decrease in amplification as a function of $H_2O_2$ concentration, FIG. 12B shows the lesions/10 kb as a funciton of $H_2O_2$ concentration. There was a 2–3-fold increase in damage to the mtDNA as compared to a nuclear gene. Since ROS generates a wide spectrum of DNA damages it was necessary to examine what types of DNA lesions inhibit the thermostable polymerase (rTth) used in these experiments. Single-strand breaks have been suggested to make up 25–50% of all damage following ROS and since single strand breaks are absolute stops to the polymerase this lesions is efficiently detected using quantiative amplification assay. We have also found that we can detect 100% of one prominent base damage lesion, thymine glycol (data not shown).

Figure 13:
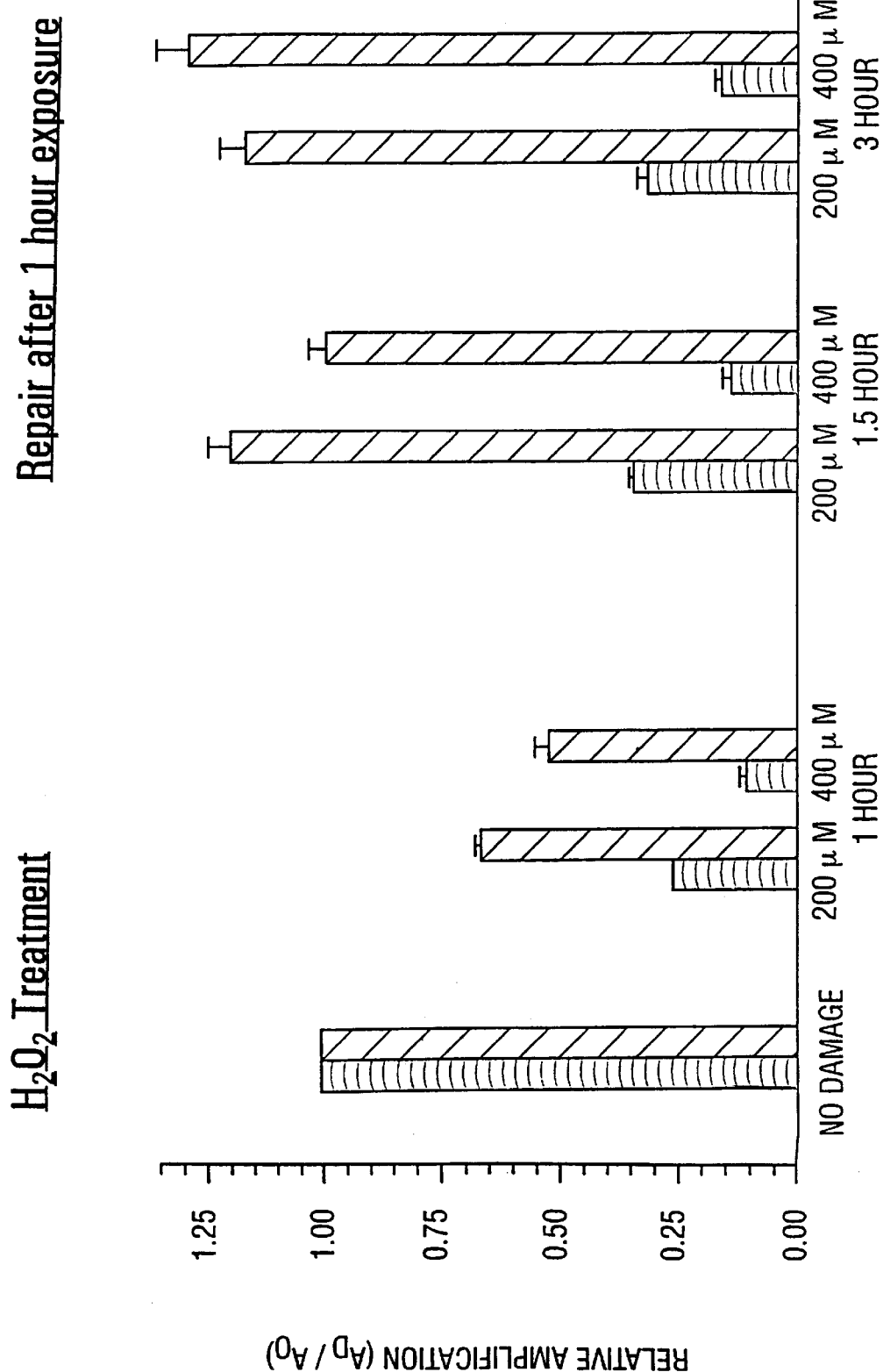
FIG. 13. Repair kinetics of oxidative DNA damage. Histograms show relative damage in the beta-globin gene and mitochondrial genome as a function of time after hydrogen peroxide treatment.

Data from a repair experiment is shown in FIG. 13. Triplicate plates of SVNF were treated with 200 or 400 μM of hydrogen peroxide ($H_2O_2$) for 1 hour. Cells were immediately harvested or were allowed 1.5 or 3 hours for repair. The DNA was extracted and used for amplification of a 16.2 kb mitochondrial fragment (open bars) and 17.7 kb β-globin gene fragment (hatched bars). These data show that the mitochondrial DNA suffers more damage than a nuclear gene and that little or no damage was repaired in the mitochondrial DNA. Note that complete repair of the β-globin gene occurs within 1.5 hours following a 1 hour $H_2O_2$ treatment.

Taken together, these data clearly show that the quantitative amplification assay can accurately measure the formation and repair of DNA damage resulting from ROS. The surprising result that mitochondrial DNA is extensively damaged and not repaired after ROS suggested that this organelle might be a critical toxicological target for ROS and other chemicals which interact with the mitochondria. If mt DNA damage is extensive and not repaired, then it would be expected to inhibit transcription of mt genes which are essential for electron transport during oxidative phosphorylation.

Glucose Oxidase-induced DNA damage in human fibroblasts. Treatment of cells with one relative high dose of $H_2O_2$, while effectively producing DNA damage, may not accurately recapitulate in vivo conditions. Therefore a $H_2O_2$ generating system, glucose oxidase (GO) was used, so that $H_2O_2$ was generated at a constant low level over a period of time. In this experiment human SVNF were treated in triplicate in serum-free media containing indicated concentrations of GO for one hour.

Figure 14:
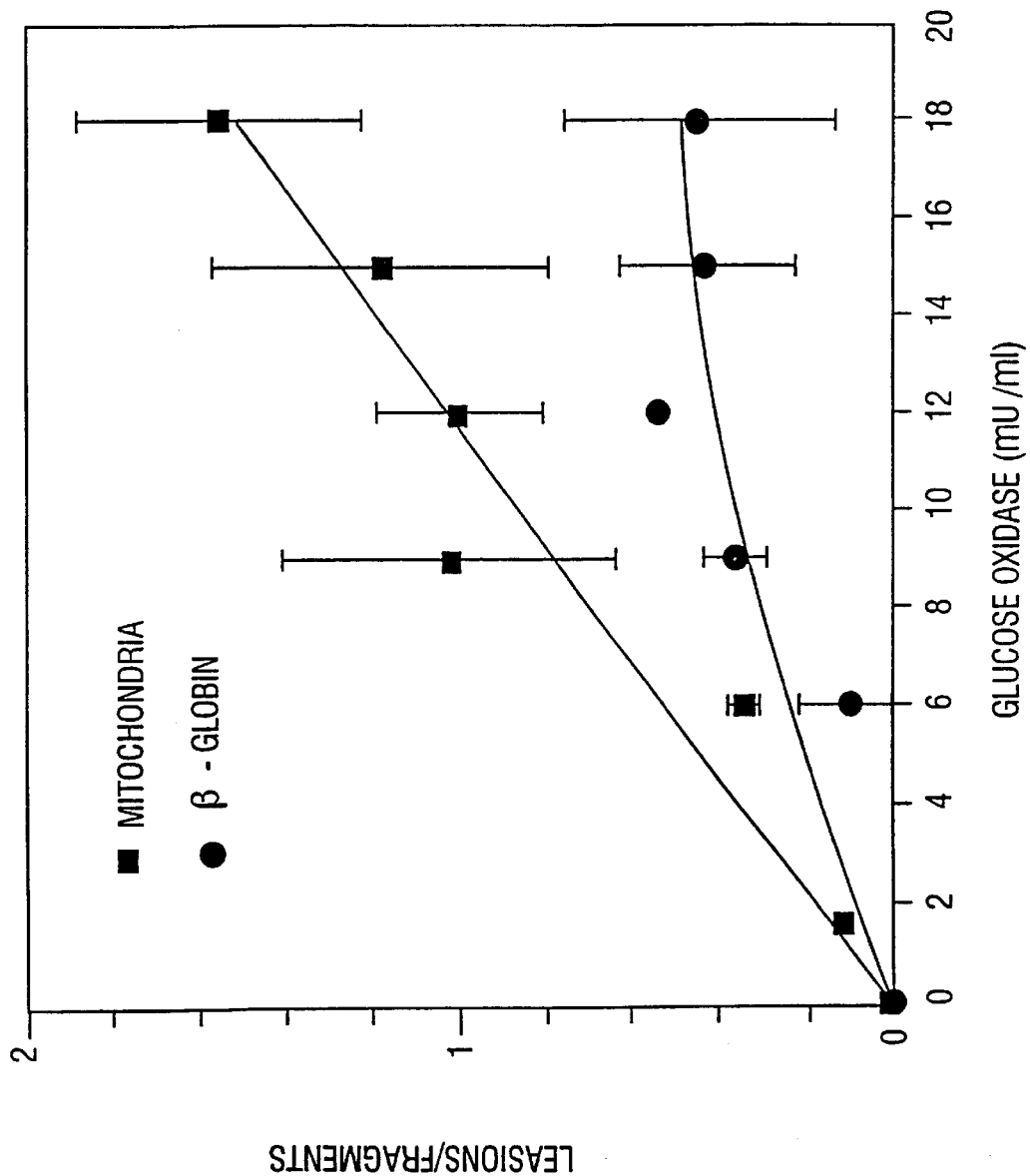
FIG. 14. Glucose oxidase-induced DNA damage in human fibroblasts. Graph shows the lesion frequencies in the beta-globin gene and mitochondrial genomes.

DNA was extracted using QIAGEN columns and the 16.2 kb mitochondrial (■) 17.7 kb β-globin (●)fragments were amplified. The relative amounts of amplification were used to calculate lesions frequencies (FIG. 14; n=4 ±S.D.). These data indicate that mt DNA is damaged more than nuclear DNA by treatment with a continuous low dose of $H_2O_2$.

Figure 15:
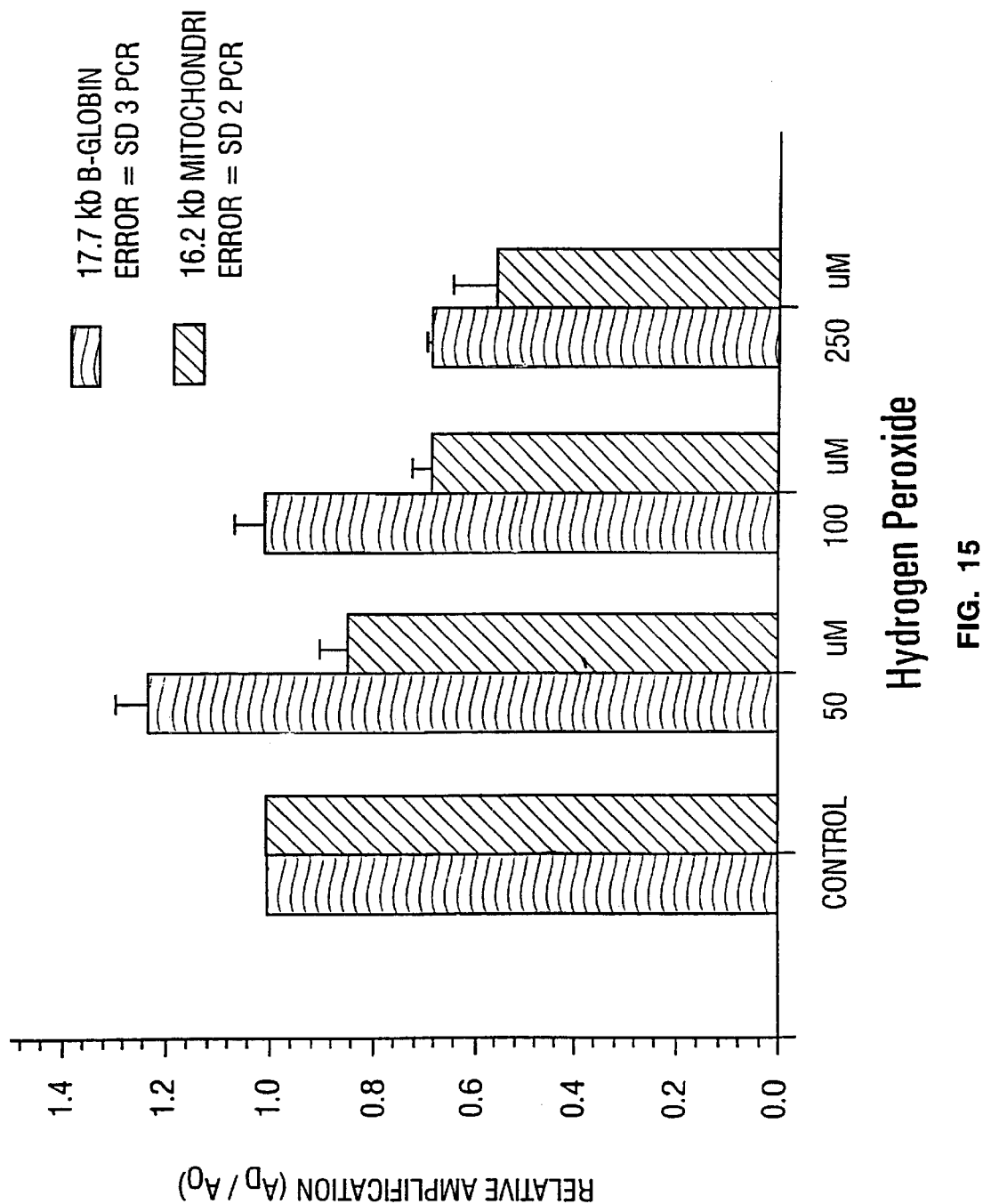
FIG. 15. Oxidative DNA damage in primary cultures of human vascular cells. Graph shows relative amplification of mitochondrial DNA versus beta-globin DNA.

Oxidative DNA damage in primary cultures of human vascular cells. In collaboration with Drs. Runge and Boor a series of experiments using human vascular cells have been initiated. In this experiment, human umbical vein endothelial cells (HUVEC) were treated with the various concentrations of $H_2O_2$ for one hour (FIG. 15). The DNA was extracted and used for QPCR of the 17.7 β-globin (open bars) and 16.2 mitochondrial DNA (hatched bars) fragments. These data indicate that like transformed fibroblasts, mtDNA in vascular endothelial cells is damaged more than nuclear DNA. These data strongly support the hypothesis that the mitochondria is a critical target for ROS-induced injury in vascular tissue.

EXAMPLE 9

Detection of 8-oxo-deoxyguanosine (8-oxoG) a Specific Oxidative DNA Adduct in Human Cells, Using the MutM Protein (FAPY Glycosylase, FPG)

Figure 16:
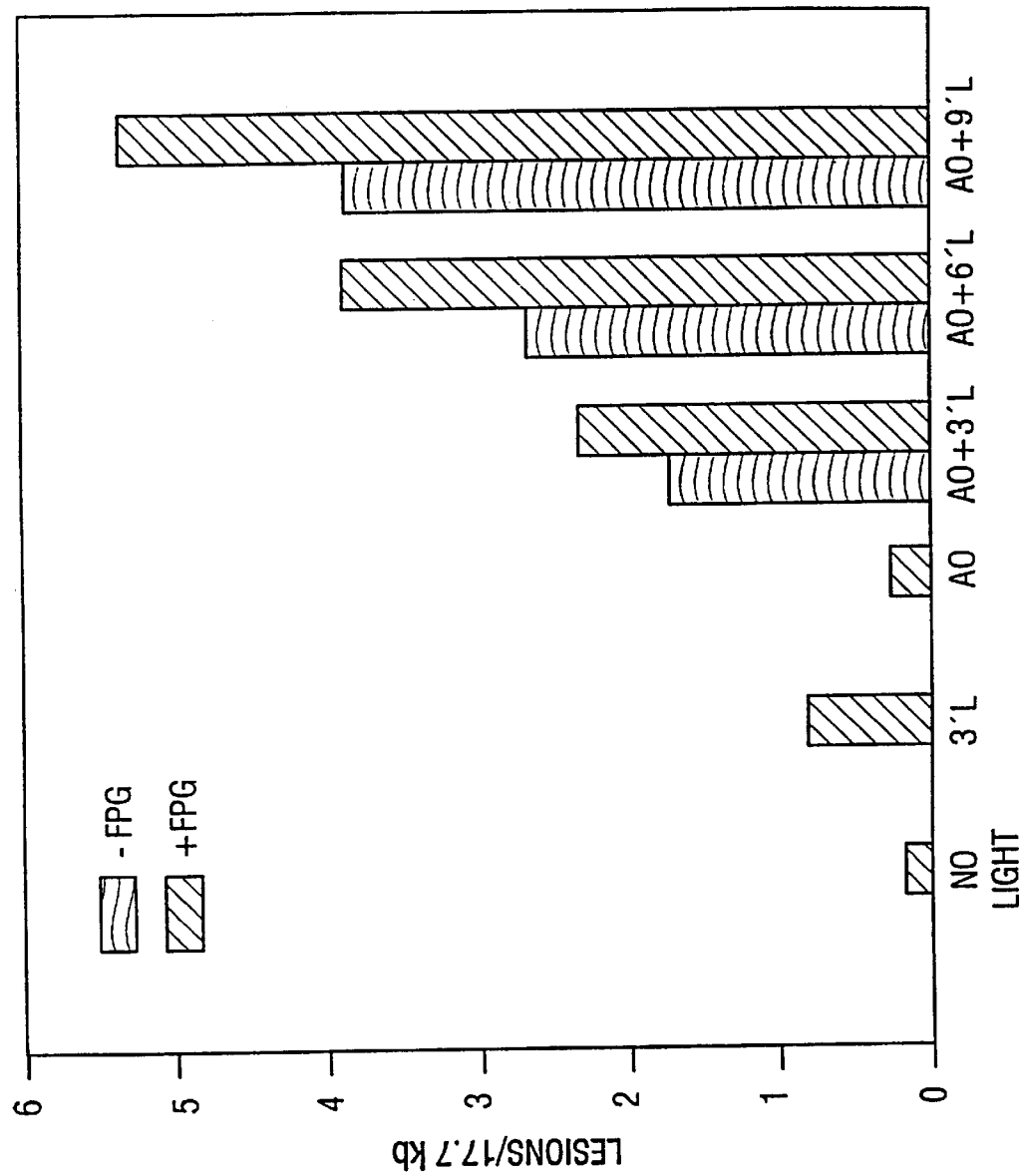
FIG. 16. Detection of 8-oxo-deoxyguanosine adducts using FPG and QPCR. Histograms show the 8-oxoG levels in untreated and acridine orange (AO) plus white light treated human cells.

Detection of FAPY glycosylase (FPG) sites in specific-gene sequences. The QPCR gene-specific assay is a robust and sensitive assay for the detection of any type of DNA damage that leads to the inhibition of a thermostable DNA polymerase. While this assay efficiently detects most forms of base damage (thymine glycol) and DNA single and double strand breaks, some DNA lesions such as 8-oxodG are not effective blocks to DNA polymerases. To directly measure these adducts in specific gene sequences, it is necessary to first convert the 8-oxodG to a strand break with a glycosylase/endonuclease from E. coli, formamidopyrimidine DNA glycosylase (FPG) (MutM protein). Besides acting on 8-oxo-deoxyguanine adducts, this enzyme also removes ring-opened purines such as formamidopyrimidine (FAPY). Data displayed in FIG. 16 were generated using DNA from cells treated with acridine orange (AO) and light (L) for 3, 6, and 9 minutes. AO plus light generates single oxygen that causes a significant amount of 8-oxodG lesions. In this experiments the DNA was extracted and an aliquot was digested with FPG. The DNA was then used in a QPCR in which the 17.7 kb β-globin fragment was amplified. The relative amount of amplification was used to determine the lesion/17.7 kb. These results are very important for at least two important following reasons. This is the first time that 8-oxodG or ring-opened purines such as formamidopyrimidine have been detected in specific gene sequences from 15 nanograms of genomic DNA. Secondly, the amount of FPG sites preexisting in cellular DNA is 0.18 lesions/17.7 kb which converts to 0.9 sites /100 kb. This is in good agreement of the number of 8-oxo-dG which can be detected in most cells grown in culture

EXAMPLE 10

Repair Kinetics of Cisplatin-DNA Adduct in Human Cells

One of the major limitations of cancer chemotherapy is delivering an effective dose of the anti-cancer drug to the target tumor. One widely used anti-cancer drug, cisplatin (cis DDP), reacts with DNA to inhibit DNA replication and results in cell death. DNA adducts resulting from cisplatin treatment, are often rapidly repaired by tumor cells and can therefore be inactivated. The development of a rapid and efficient method for the quantitation of cisplatin-DNA adducts in patients undergoing cisplatin chemotherapy would allow more beneficial treatment strategies. Data in FIGS. 17A and 17B show the repair kinetics of transformed human fibroblasts which have been treated with cisplatin (150 µM) for 2 hours and then allowed various time periods for repair (β-globin (FIG. 17A) and hprt (FIG. 17B)). The DNA was extracted and used for the long amplification. Note that cisplatin-DNA adducts are repaired slowly as compared to UV damaged DNA.

EXAMPLE 11

Detection of Benzo[a]Pyrene Diol Epoxide-DNA Adducts in Human Cells. DNA

Figure 18A:
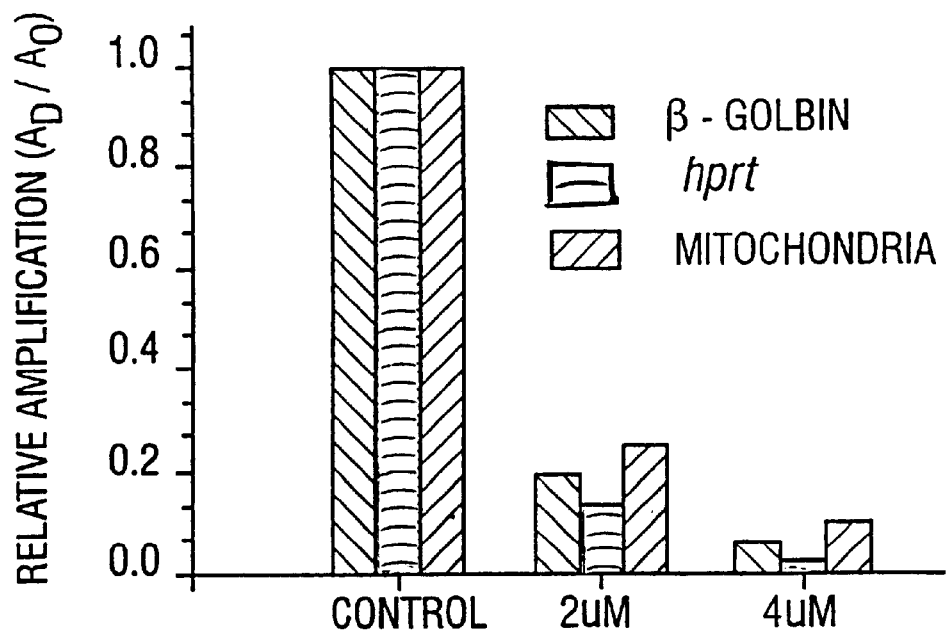
FIGS. 18A and 18B. Detection of benzo[a]pyrene diol epoxide-DNA adducts in human cells. Human cells were treated with benzo[a]pyrene diol epoxide (BPD) for one hour and the DNA was used for amplification of either mitochondria, hprt or beta-globin fragments.
Figure 18B:
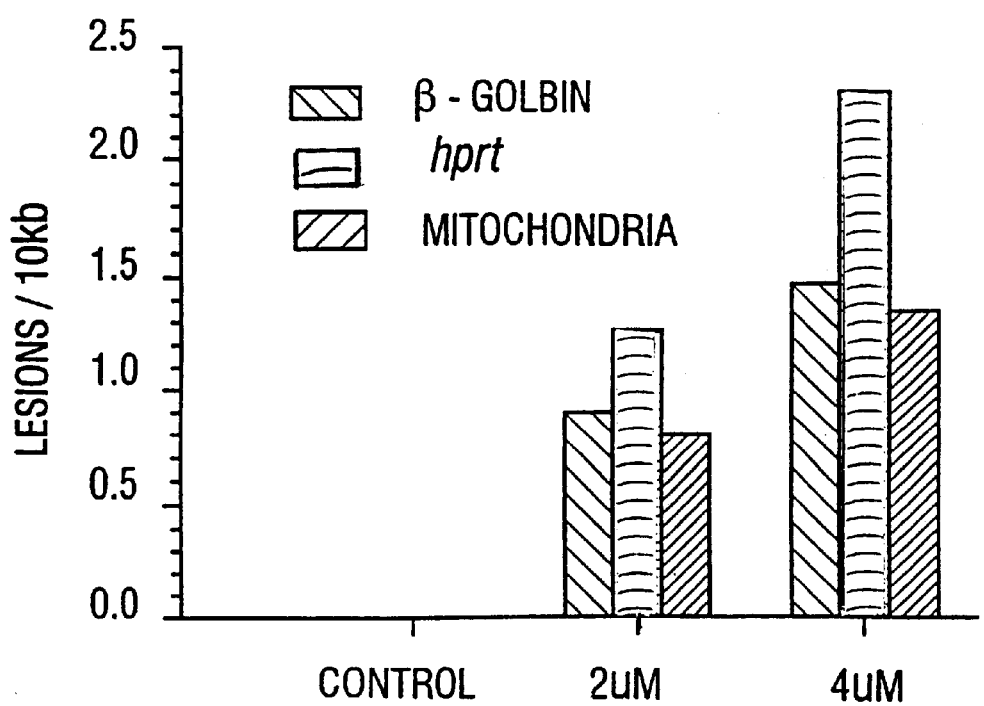

Many environmental chemical pollutants can cause cancer in experimental animals. One such compound, benzo[a]pyrene diol epoxide (BPDE), is produced by combustion of fossil fuels and is found in cigarette smoke. BPDE is one of the most potent carcinogens known to man. Data in FIGS. 18A and 18B show the production of BPDE-DNA adducts in three different genomic regions in transformed human cells. Cells were treated with BPDE (none, 2 µM and 4 µM) and the DNA was used for quantitative amplification of long DNA fragments.

While the above description contains many specifics, these should not be construed as limitations on the scope of the invention, but rather as exemplifications of preferred embodiments. Many other potential variations are possible, as would be apparent to one skilled in the art. Accordingly, the scope of the invention should be determined by the scope of the appended claims and their legal equivalents, and not just by the embodiments.

The following citations are incorporated in pertinent part by reference herein for the reasons cited in the above text.

REFERENCES

Barnes WM. PCR amplification of up to 35-kb DNA with high fidelity and high yield from lambda bacteriophage templates. *Proceedings of the National Academy of Sciences of the United States of America.* 91(6):2216–20, Mar 15, 1994.

Bohr and Okumoto, In Friedberg and Hanawalt, "DNA Repair:
A Laboratory Manual of Research Procedures," Marcel Dekker, New York, 3:347–366, 1988.

Chandrasekhar and Van Houten, *J. Mol. Biol.*, 238:319–332, 1994.

Cheng et al. Effective amplification of long targets from cloned inserts and human genomic DNA. *Proceedings of the National Academy of Sciences of the United States of America.* 91(12):5695–9, Jun. 7, 1994.

Cheng et al. Complete mitochondrial genome amplification [letter]. *Nature Genetics.* 7(3) :350–1, July 1994.

Cheng et al. *Nature.* 369(6482):684–5, Jun. 23, 1994.

Govan et al., *Nucleic Acids Res.*, 18:3823–3829, 1990.

Jennerwein and Eastman, *Nucleic Acids Res.*, 19:6209–6214, 1991.

Kalinowski et al., *Nucleic Acids Res.*, 20:3485–3494, 1992.

Katz et al., *Amplifications* (Perkin Elmer), 8:10–13, 1992.

Mellon et al., *Cell,* 51:241–249, 1987.

Mellon and Hanawalt, *Nature,* 342:95–98, 1989.

Smerdon and Thoma, *Cell,* 61:675–684, 1990.

Van Houten et al., *Amplifications* (Perkin Elmer), 10:10–17, 1993.

I claim:

1. A method for diagnosing efficacy of an anti-neoplasia therapy in a patient comprising the steps of:
   obtaining samples of a double-stranded DNA template from a patient prior to therapy and at least one subsequent time;
   processing each sample separately, wherein the first and second complementary strands of said DNA each have a strand-specific primer site, and wherein said primer-sites are separated by at least about 5000 base pairs;

processing the control DNA template from prior to therapy by combining the first and second complementary strands in a mixture with primers to said strand-specific primer-sites on each of the complementary strands;

performing quantitative long DNA amplification on the mixture;

repeating the above steps with an amount of said test double-stranded DNA template from after therapy, which has been subjected to DNA-damaging or potentially DNA-damaging conditions during therapy; and assessing DNA damage in each sample by determining a lower amplification rate for test DNA as compared to control DNA, wherein therapeutical efficacy is directly proportional to DNA damage assessed in the sample obtained at said subsequent time.

2. A personal DNA genotoxin exposure dosimeter comprising:

at least two double-stranded template samples, having DNA primer sites separated by at least 5,000 base pairs, at least one sample being exposurable to an environment and one sample being a control sealed from the environmental exposure; and a means for attaching said dosimeter to a person.

3. A method of monitoring an individual's exposure to genotoxins in an environment over an interval of time comprising the steps of:

attaching the dosimeter of claim 2 to said individual;

exposing at least one DNA sample to said environment;

subjecting said DNA samples to amplification with primers for the primer sites; and assessing genotoxin exposure by determining any decrease in amplification rate resulting from the environmental exposure.

4. A method of detecting DNA damage resulting in 8-oxo-deoxyguanosine or formamidopyrimidine, the method comprising:

obtaining a first double-stranded DNA template with first and second complementary DNA strands, the first and second complementary strands each having a strand-specific primer site and the primer sites being separated by at least about 5,000 base pairs;

reacting a portion of the first double-stranded DNA template with glycosylase/endonuclease or formamidopyrimidine DNA glycosylase to convert DNA damage into a strand break, resulting in a second double-stranded DNA template sample;

combining the first and second complementary strands of the first sample and the second sample separately with primers to the strand-specific primer sites on each of the complementary strands;

performing long DNA amplification on the control sample and the test sample;

assessing DNA damage due to formation of 8-oxo-deoxyquanosine or formamidopyrimidine by observing decreases in the rate of DNA amplification of the second sample as compared to the first sample.

5. A method of assessing DNA damage induced by cis-platin, the method comprising:

obtaining a first DNA template sample from a patient subject to cis-platin therapy, the sample comprising double-stranded DNA template with a first and second complementary DNA strand, the first and second complementary strands each having a strand-specific primer site and the primer sites being separated by at least 5,000 base pairs;

reacting a portion of the first DNA template with an amount of cyanide ion displacing cis-platin adducts from the DNA to form a second DNA template;

separately combining the first and second complementary DNA strands from the first and second DNA templates with primers to the strand-specific primer site on each of the complementary strands;

performing quantitative long-DNA amplification on the first and the second DNA templates;

wherein the second template is a control and decreased rate of amplification of the first DNA template as compared to the control DNA is a measure of cis-platin-induced DNA damage.

* * * * *

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 1, line 43, "including" should read --include--.

In Column 1, line 44, please insert a dash before "the requirements".

In Column 1, line 46, please insert a dash before "the need".

In Column 1, line 53, "causes" should read --cause--.

In Column 1, line 53, please remove the word "in" between the words "cause" and "a decrease".

In Column 1, line 63, please insert a line before "Limitation".

In Column 1, line 65, please insert a line before "Current PCR".

In Column 2, line 22, "derive" should read --derived--.

In Column 2, line 57, "50 to" should read --50- to--.

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 2, line 57, "100 fold" should read --100-fold--.

In Column 3, line 25, "damate" should read --damage--.

In Column 3, line 55, please insert the word --and-- before the word "comparing".

In Column 4, line 32, "geneotoxin" should read --genotoxin--.

In Column 4, line 37, "geneotoxin" should read --genotoxin--.

In Column 4, line 60, "damae" should read --damage--.

In Column 5, line 12, "hypoxanthine phosphoribosyltransferase" should be italicized.

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 5, line 13, "(hprt)" should be italicized.

In Column 5, line 15, "hprt" should be italicized.

In Column 5, line 26, "hprt" should be italicized.

In Column 5, line 41, "two-times" should read --two times--.

In Column 5, line 43, "hprt" should be italicized.

In Column 5, line 56, "hprt" should be italicized.

In Column 5, line 61, please insert the word --in-- between the words "cancer" and "a homozygous".

In Column 5, line 62, "hPMS2" should be italicized.

In Column 5, line 64, "hMSH2" should be italicized.

In Column 6, line 22, "hprt" should be italicized.

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 8, line 6, please remove the comma after "ECL".

In Column 8, line 47, "above. Then" should read --above, then--.

In Column 9, line 49, "Examples" should read --examples--.

In Column 9, line 57, in Table 1, "hprt" should be italicized.

In Column 9, line 63, in Table 1, please insert a line between the line ending with "human" and the line beginning with "Inactive".

In Column 11, line 24, please insert a line before "Isolation of genomic DNA".

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 11, line 36, please insert a line before "Digestion of genomic DNA".

In Column 11, line 49, "hprt" should be italicized.

In Column 11, line 52, "hprt" should be italicized.

In Column 11, line 65, please insert a comma between the words "seconds" and "a combination".

In Column 12, line 7, "hprt" should be italicized.

In Column 12, line 26, "hprt" should be italicized.

In Column 12, line 29, "hprt" should be italicized.

In Column 12, line 39, please insert a line before "Various length".

In Column 12, line 60, "($A_D$)" should read --($A_D$)--.

In Column 12, line 61, "($A_o$)" should read --($A_O$)--.

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 12, line 63, please remove the hard return after the word "equation".

In Column 12, line 63, "$|f(x)=e^{-\lambda}\lambda^x/x!|$" should not be italicized.

In Column 12, line 66, please remove the two hard returns before the words "for the zero".

In Column 13, line 2, "$A_D$" should read --$A_D$--.

In Column 13, line 2, "$A_O$" should read --$A_O$--.

In Column 13, line 7, "$A_{UV}/A_O$, where $A_{UV}$" should read --$A_{UV}/A_O$, where $A_{UV}$--.

In Column 13, line 8, "$A_O$" should read --$A_O$--.

In Column 13, line 17, "hprt" should be italicized.

In Column 13, line 49, "hprt" should be italicized.

In Column 13, line 62, "±S.D." should read --± S.D.--.

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 13, line 66, "hprt" should be italicized.

In Column 14, line 7, please begin a new paragraph after the word "lines." and before the words "In order".

In Column 14, line 8, please insert a comma between the words "assay" and "the".

In Column 14, lines 21-22, "EDTA). The DNA is" should read --EDTA) and is--.

In Column 14, line 27, "are" should be changed to --were--.

In Column 14, line 34, "($A_o$)" should read --$A_o$--.

In Column 14, line 36, please remove the two hard returns after the word "equation".

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 14, line 36, "|$f(x)=e^{-\lambda}\lambda^x/x!$|" should not be italicized.

In Column 14, line 40, please remove the two hard returns before the words "for the zero".

In Column 14, line 40, "(ie," should read --(i.e.,--.

In Column 14, line 43, "$A_D/A_O$" should read --$A_D/A_O$--.

In Column 14, line 44, please indent before the words "Repair of".

In Column 14, line 46, "hprt" should be italicized.

In Column 14, line 47, "±SEM" should read --± SEM--.

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 14, line 49, "$t_{1/2}23.5$" should read --$t_{1/2}$ 23.5--.

In Column 14, line 50, "$t_{1/2}=8.3$" should read --$t_{1/2} = 8.3$--.

In Column 14, line 51, "hprt" should be italicized.

In Column 14, line 52, "$t_{1/2}=5.0$" should read --$t_{1/2} = 5.0$--.

In Column 14, line 54, please remove the words "These include:".

In Column 14, line 58, "hPMS2" should be italicized.

In Column 14, line 60, "hMSH2" should be italicized.

In Column 15, line 10, please insert a new line between the words "Detection" and "Simultaneous".

In Column 15, line 28 "have" should read --has--.

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 15, line 46, "is not" should read --are not--.

In Column 16, line 1, please begin a new paragraph before the words "Reactive oxygen".

In Column 16, line 10, please remove the word "a" before the word "QIAGEN".

In Column 16, line 23, "lesions" should read --lesion--.

In Column 16, line 52, please begin a new paragraph before the words "Treatment of cells".

In Column 16, line 56, "were" should read --was--.

In Column 16, line 63, "lesions" should read --lesion--.

In Column 16, line 63, "4±S.D." should read --4 ± S.D.--.

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 16, line 67, please begin a new paragraph before the words "In collaboration with".

In Column 18, line 19, please insert a line between the line ending with "DNA fragments." and the line beginning with "While the above."

In Column 18, line 32, please insert a comma after the word "Barnes".

In Column 18, line 32, "WM." should read –Wm.--.

In Column 18, line 37, please remove the hard return after the word "Repair:".

In Column 19, line1, "primer-" should read --primer--.

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 19, line 6, "primer-sites" should read --primer sites--.

In Column 19, line 8, "long DNA" should read --long-DNA--.

In Column 19, line 37, "envi-" should read --envir---.

In Column 20, line 14, "long DNA" should read --long-DNA--.

In Column 20, line 21, "cis-platin" should read --cisplatin--.

In Column 20, line 23, "cis-platin" should read --cis platin--.

In Column 20, line 30, "cis-platin" should read --cis platin--.

UNITED STATES PATENT AND TRADEMARK OFFICE
CERTIFICATE OF CORRECTION

PATENT NO. : 5,989,816
DATED : November 23, 1999
INVENTOR(S) : Bennet Van Houten It is certified that error appears in the above-identified patent and that said Letters Patent is hereby corrected as shown below:

In Column 20, line 40, "cis-platin" should read --cis platin--.

Signed and Sealed this

Twenty-second Day of May, 2001

Attest:

NICHOLAS P. GODICI

*Attesting Officer*  *Acting Director of the United States Patent and Trademark Office*